(12) United States Patent
Payne et al.

(10) Patent No.: US 9,107,974 B2
(45) Date of Patent: Aug. 18, 2015

(54) HONEY IMPREGNATED COMPOSITE DRESSING HAVING SUPER ABSORBENCY AND INTELLIGENT MANAGEMENT OF WOUND EXUDATE AND METHOD OF MAKING SAME

(71) Applicant: LINKS MEDICAL PRODUCTS INCORPORATED, Irvine, CA (US)

(72) Inventors: Howard Kenneth Payne, Horsham (GB); Gregory Frank Devenish, Hampshire (GB)

(73) Assignee: LINKS MEDICAL PRODUCTS, INC, Irvine, CA (US)

( * ) Notice: Subject to any disclaimer, the term of this patent is extended or adjusted under 35 U.S.C. 154(b) by 0 days.

(21) Appl. No.: 14/642,664

(22) Filed: Mar. 9, 2015

(65) Prior Publication Data
US 2015/0174284 A1    Jun. 25, 2015

Related U.S. Application Data

(63) Continuation-in-part of application No. 29/511,393, filed on Dec. 10, 2014, and a continuation-in-part of application No. 13/939,829, filed on Jul. 11, 2013.

(51) Int. Cl.
*A61F 13/15* (2006.01)
*A61M 27/00* (2006.01)
(Continued)

(52) U.S. Cl.
CPC ............ *A61L 15/40* (2013.01); *A61F 13/0209* (2013.01); *A61F 13/0223* (2013.01);
(Continued)

(58) Field of Classification Search
CPC ............ A61F 2013/00314; A61F 2013/00331; A61F 2013/00161; A61F 2013/00285

USPC .................. 604/360, 308, 543, 367, 379, 380
See application file for complete search history.

(56) References Cited

U.S. PATENT DOCUMENTS 3,767,784 A    10/1973    Gluck
4,231,357 A    11/1980    Hessner
(Continued)

OTHER PUBLICATIONS

Molan, P.C.; The Role of Honey in Management of Wounds; Journal of Wound Care; Sep., vol. 8, No. 8 pp. 415-418 (1999); MA Healthcare Ltd.; London, United Kingdom. Accessed Aug. 21, 2014. Available from http://researchcommons.walkato.ac.nz/bitstream/handle/10289/2041/The%20role%20%20honey.pd?sequence=1.

(Continued)

*Primary Examiner* — Jacqueline Stephens
(74) *Attorney, Agent, or Firm* — Jerry R. Potts; James McDaniel

(57) ABSTRACT

A super absorbent, honey-dosed foam/fiber composite, gap patterned wound dressing, comprising: a patterned foam/fiber composite structure having a gap patterned side and a non-gap patterned side, wherein the patterned side includes a pattern of foam/fiber gaps disposed between foam/fiber areas dosed with honey, where the pattern of foam/fiber gaps is formed by the honey-dosed areas, such that the patterned foam/fiber composite structure includes a layer of super absorbent material located substantially adjacent to the honey-dosed areas; and wherein a wound in contact with the gap patterned side discharges an exudate which substantially collects in the individual ones of the foam/fiber gaps causing honey in the individual ones of the honey-dosed areas to be substantially dispersed throughout a wound treatment zone and a portion of the exudate that is collected in the individual ones of the foam/fiber gaps is transferred to and collected in the super absorbent material.

12 Claims, 21 Drawing Sheets

(51) Int. Cl.
*A61L 15/40* (2006.01)
*A61F 13/02* (2006.01)
*A61L 15/60* (2006.01)
*A61F 13/00* (2006.01)

(52) U.S. Cl.
CPC ........ *A61F 13/0253* (2013.01); *A61F 13/0289* (2013.01); *A61L 15/60* (2013.01); *A61F 2013/00314* (2013.01); *A61F 2013/00331* (2013.01)

(56) References Cited

U.S. PATENT DOCUMENTS

| | | | |
|---|---|---|---|
| 4,341,207 A | 7/1982 | Steer et al. | |
| D278,363 S | 4/1985 | Schenkel et al. | |
| 4,552,138 A | 11/1985 | Hofeditz et al. | |
| 4,649,909 A | 3/1987 | Thompson | |
| 5,086,764 A | 2/1992 | Gilman | |
| 5,527,271 A | 6/1996 | Shah et al. | |
| 5,939,339 A | 8/1999 | Delmore et al. | |
| 6,605,751 B1 | 8/2003 | Gibbins et al. | |
| 6,967,261 B1 | 11/2005 | Soerens et al. | |
| 7,005,556 B1 | 2/2006 | Becker et al. | |
| 7,220,889 B2 | 5/2007 | Sigurjonsson et al. | |
| 7,714,183 B2 | 5/2010 | Caskey | |
| RE42,755 E | 9/2011 | Molan | |
| 8,067,662 B2 | 11/2011 | Aali et al. | |
| 2003/0120229 A1* | 6/2003 | de Jong et al. | 604/367 |
| 2006/0149182 A1 | 7/2006 | Cullen et al. | |
| 2008/0014386 A1 | 1/2008 | Murphy et al. | |
| 2008/0027366 A1 | 1/2008 | Da Silva Macedo, Jr. | |
| 2011/0135726 A1 | 6/2011 | Munro et al. | |
| 2014/0127283 A1 | 5/2014 | Watson | |
| 2014/0142522 A1 | 5/2014 | Filippova et al. | |

OTHER PUBLICATIONS

Technical University of Liberec Wound Care, Oct. 2006. The Technical University of Liberec, Liberec, Czech Republic. Accessed Aug. 25, 2014. Available form http://www.ft.tul.cz/depart/knt/nove/dokumenty/studmaterial/zt/prednasky/wound_care.pdf.

* cited by examiner

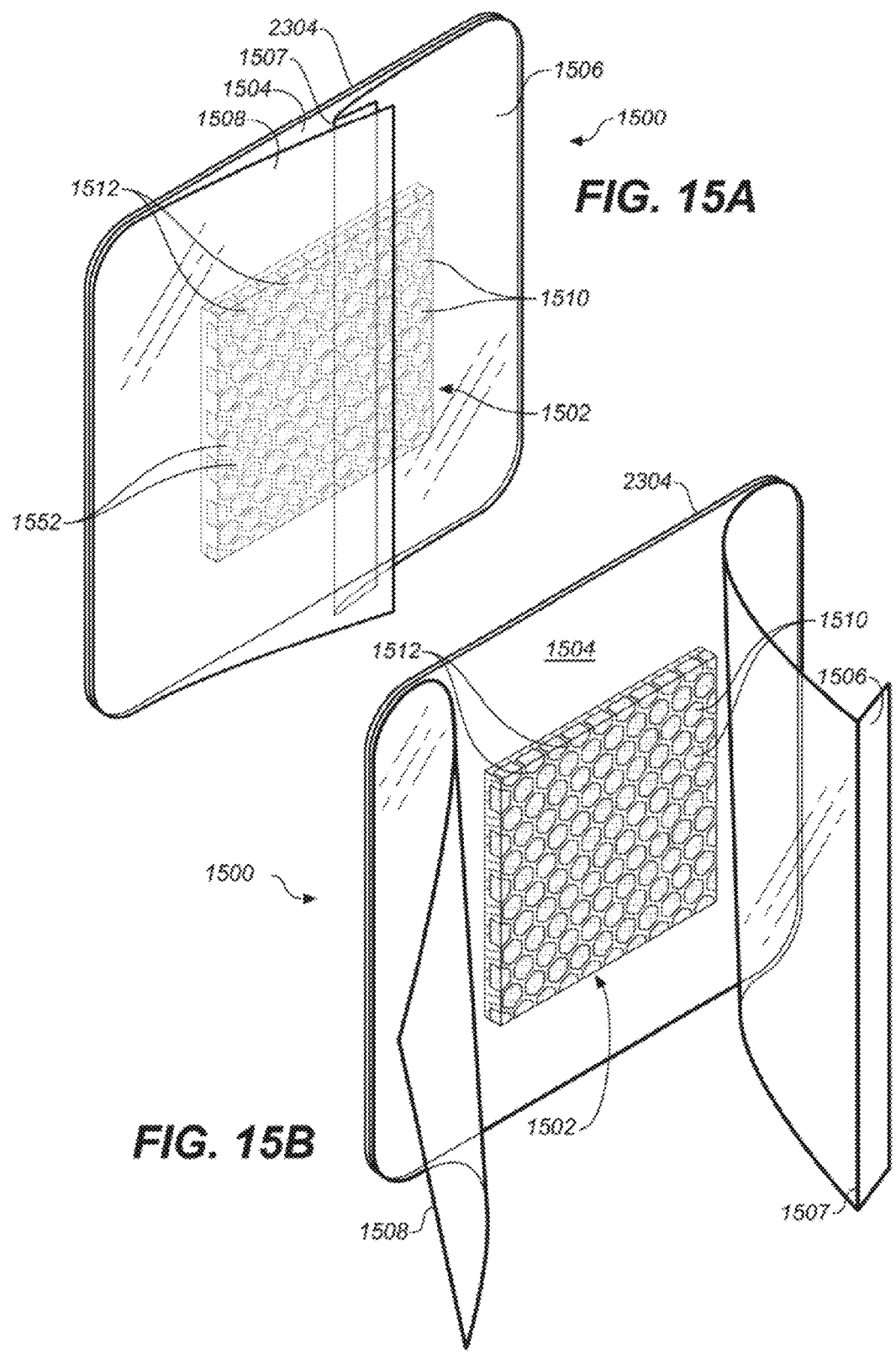

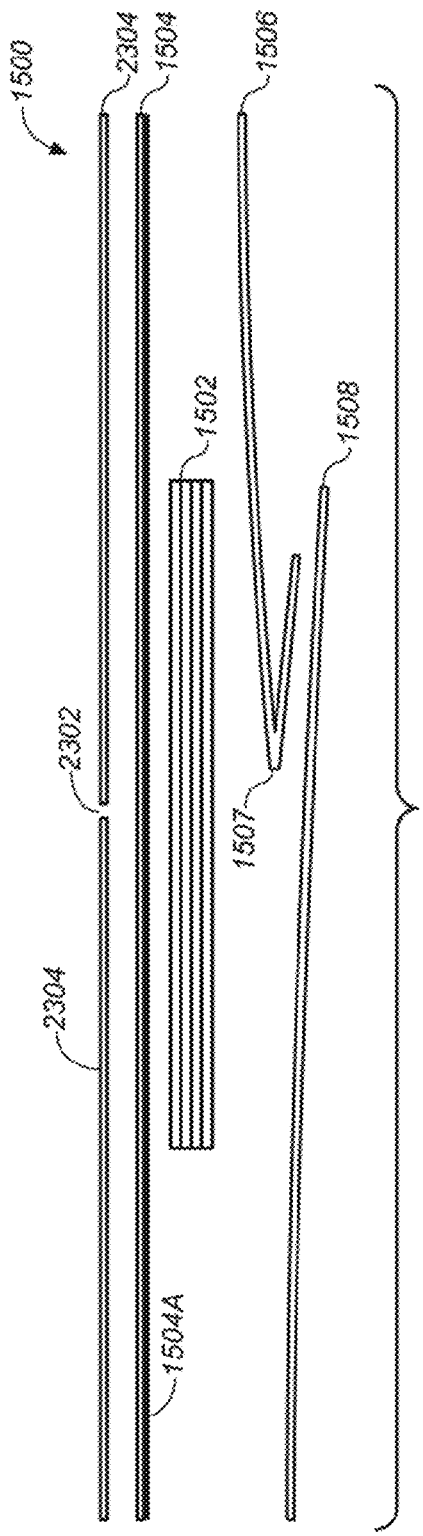
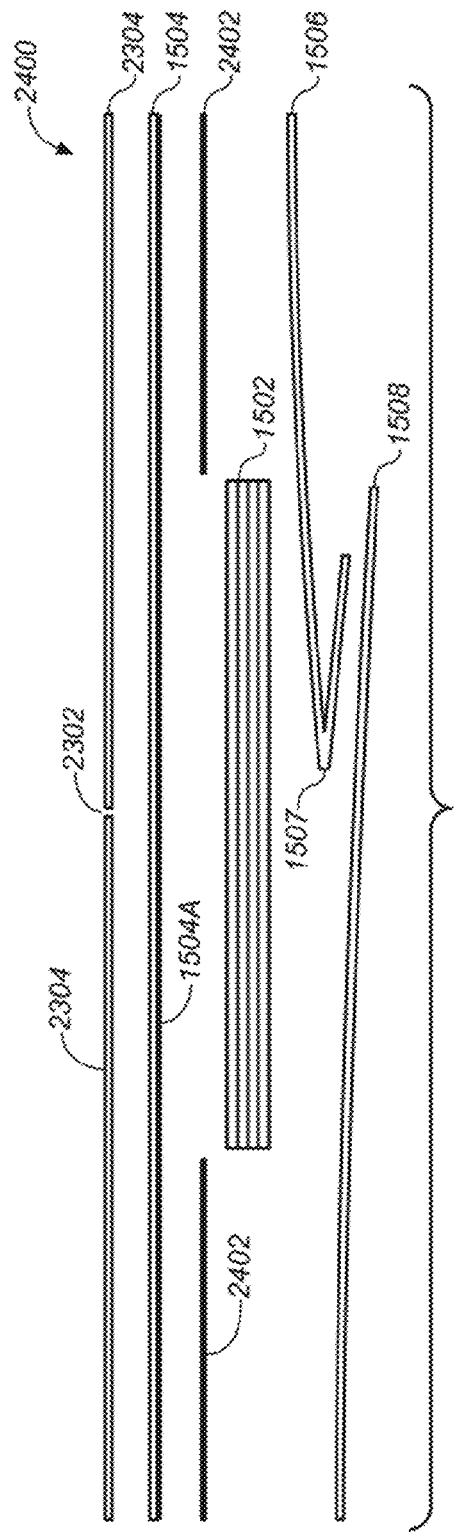

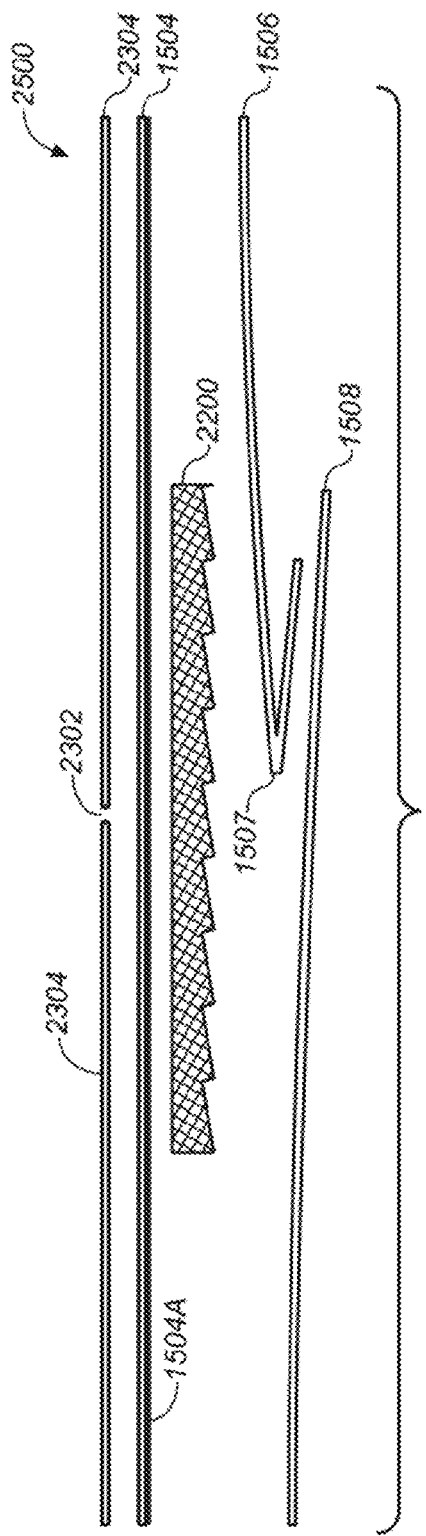
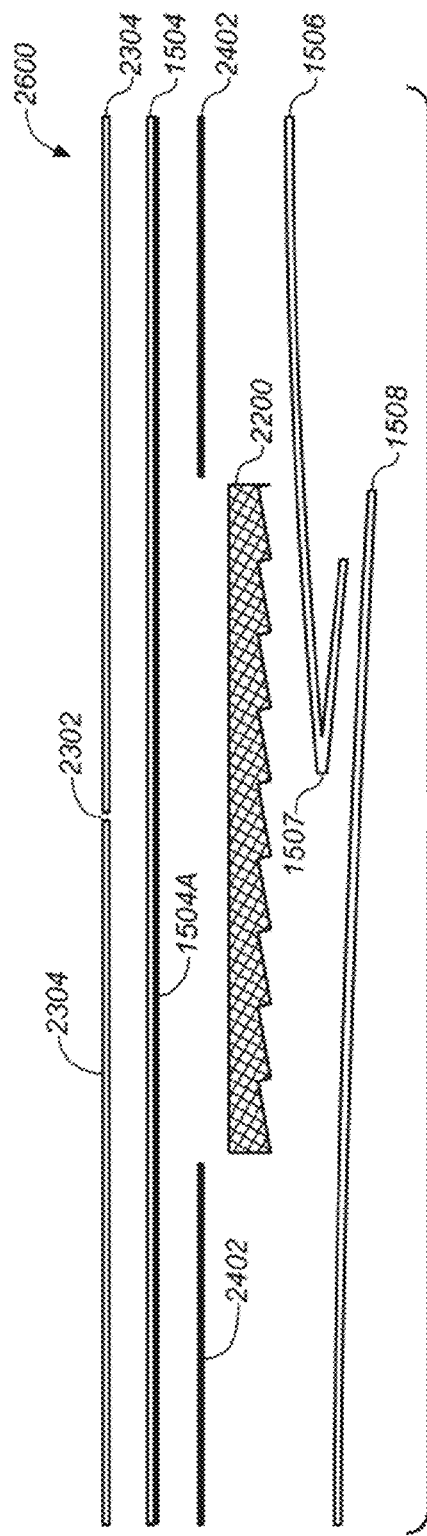

HONEY IMPREGNATED COMPOSITE DRESSING HAVING SUPER ABSORBENCY AND INTELLIGENT MANAGEMENT OF WOUND EXUDATE AND METHOD OF MAKING SAME

CROSS-REFERENCE TO A RELATED APPLICATION

This application is a continuation-in-part of U.S. patent application Ser. No. 13/939,829, filed Jul. 11, 2013; and a continuation-in-part of U.S. patent application Ser. No. 29/511,393, filed on Dec. 10, 2014.

FIELD OF THE INVENTION

This invention relates generally to medical grade composite dressings and more particularly to a gap-patterned, medical grade honey bearing composite dressing having super absorbency and intelligent management of wound exudate.

BACKGROUND OF THE INVENTION

Prior to the present invention, as set forth in general terms above and more specifically below, it is known, to employ various dressing designs for applications to wounds. See for example, U.S. Pat. No. 3,767,784 by Gluck, U.S. Pat. No. 4,231,357 by Hessner, U.S. Pat. No. 4,649,909 by Thompson, U.S. Pat. No. 5,086,764 by Gilman, U.S. Pat. No. 6,605,751 by Gibbins, et al., U.S. Pat. No. 6,697,261 by Soerens, at al., U.S. Pat. No. 7,220,889 by Sigurjonsson, et al., U.S. Pat. No. 7,714,183 by Caskey, U.S. Patent Application Publication 2008/0027366 by De Silva Macedo, Jr., U.S. Patent Application Publication 2011/0135726 by Munro, et al., U.S. Patent Application Publication 2014/0127283 by Watson, U.S. Patent Application Publication 2014/0142522 by Filippova, at al., and U.S. Pat. RE 42,755 E by Molan. While these various wound dressings may have been generally satisfactory, there is nevertheless a need for a new and improved super absorbent, honey bearing composite wound dressing having super absorbency with intelligent management of wound exudates where the honey in the honey bearing areas of the wound dressing is delivered to a wound treatment area under force of exudates in the wound treatment area flowing from the wound treatment area into the composite dressing and then be transferred to and collected in a super absorbent material.

It is a purpose of this invention to fulfill this and other needs in the art in a manner more apparent to the skilled artisan once given the following disclosure.

SUMMARY OF THE INVENTION

A first aspect of the present invention is a honey bearing composite wound dressing having super absorbency with intelligent management of wound exudates, comprising a patterned foam/fiber composite structure having a gap patterned side and a non-gap patterned side, wherein the patterned side includes a pattern of foam/fiber gaps disposed between foam/fiber areas dosed with honey, where the pattern of foam/fiber gaps is formed by the honey-dosed areas, such that the patterned foam/fiber composite structure includes a layer of super absorbent material located substantially adjacent to the honey-dosed areas; and wherein a wound in contact with the gap patterned side discharges an exudate which substantially collects in the individual ones of the foam/fiber gaps causing honey in the individual ones of the honey-dosed areas to be substantially dispersed throughout a wound treatment zone and a portion of the exudate that is collected in the individual ones of the foam/fiber gaps is transferred to and collected in the super absorbent material.

In one embodiment of the first aspect of the present invention, individual ones of the honey-dosed areas are hexagon-shaped areas.

In another embodiment of the first aspect of the present invention, the super absorbent material is a medical-grade, super absorbent polymer.

In another embodiment of the first aspect of the present invention, the super absorbent material is a medical-grade, super absorbent powder.

In yet another embodiment of the first aspect of the present invention, the wound dressing is further comprised of a bacterial barrier layer having a proximal side and a distal side wherein the non-gap patterned side of the patterned foam/fiber composite is located substantially adjacent to the proximal side of the bacterial barrier layer.

In still yet another embodiment of the first aspect of the present invention, the bacterial barrier layer is a medical-grade, breathable material which has an adhesive coating substantially applied to the proximal side.

In yet another embodiment of the first aspect of the present invention, the wound dressing has a removable liner located substantially adjacent to the distal side of the bacterial barrier material.

In another embodiment of the first aspect of the present invention, the removable liner is medical grade, polyethylene.

In yet another embodiment of the first aspect of the present invention, the wound dressing is further comprised of a removable liner located substantially adjacent to the proximal side of the bacterial barrier material and substantially enclosing the patterned foam/fiber composite, wherein the removable liner is a medical grade, high density polyethylene.

In yet another embodiment of the first aspect of the present invention, the patterned foam/fiber composite structure has a thickness in a range of between 0.05 mm to about 100 mm.

In still yet another embodiment of the first aspect of the of the present invention, the wound dressing is further comprised of a gel adhesive layer wherein the gel adhesive layer is located substantially adjacent to the foam/fiber composite and the proximal side of the bacterial barrier material.

In yet another embodiment of the first aspect of the present invention, the gel adhesive layer is a silicone gel adhesive.

A second aspect of the present invention is a honey bearing composite wound dressing having super absorbency with intelligent management of wound exudates, comprising a foam/fiber layer having a gap patterned side and a non-gap patterned side, wherein the patterned side includes a pattern of foam/fiber gaps disposed between foam/fiber areas dosed with honey, where the pattern of foam/fiber gaps is formed by the honey-dosed areas; a super absorbent material layer having a proximal side and a distal side wherein the proximal side of the super absorbent material is located adjacent to the non-gap patterned side of the foam/fiber layer; and a non-woven material layer having a proximal side and a distal side wherein the proximal side of the non-woven layer is located adjacent to the distal side of the super absorbent material layer.

In one embodiment of the second aspect of the present invention, the foam/fiber layer is a medical grade, polyether polyurethane foam with a polyolefin fiber matrix.

In another embodiment of the second aspect of the present invention, the super absorbent material layer is a medical-grade, super absorbent polymer.

In another embodiment of the second aspect of the present invention, the super absorbent material layer is a medical-grade, super absorbent powder.

In another embodiment of the second aspect of the present invention, the foam/fiber layer has a thickness in a range of between 0.05 mm to about 100 mm.

In yet another embodiment of the second aspect of the present invention, the bacterial barrier layer is a medical-grade, breathable material which has an adhesive coating substantially applied to the proximal side.

In still yet another embodiment of the second aspect of the present invention, the non-woven material includes a medical-grade, non-woven material.

In yet another embodiment of the second aspect of the present invention, the non-woven material includes a discontinuous hot-melt thermal adhesive coating conventionally applied to one face of the non-woven material.

In a third aspect of the present invention is a method for preparing a super absorbent, honey-dosed foam/fiber composite, gap patterned wound dressing, comprising the steps of: placing a layer of super absorbent material substantially over a layer of foam/fiber material; placing a layer of a non-woven material substantially over the layer of super absorbent material; preparing and placing a layer of a bacterial barrier material substantially over the layer of non-woven material; placing a casting layer substantially over the layer of bacterial barrier material; heating the layers of foam/fiber, super absorbent material, non-woven material, the bacterial barrier layer, and casting layer to substantially join the layers of foam/fiber, super absorbent material, non-woven material, the bacterial barrier layer, and the casting layer together; applying specific amounts of honey to the layer of foam/fiber material to substantially dose a portion of the layer of foam/fiber material with the honey; placing a liner layer substantially over the heat sealed layers of honey-dosed foam/fiber, super absorbent material, non-woven material, bacterial barrier layer, and casting liner such that the liner layer is substantially adjacent to the honey-dosed foam/fiber material; cutting the heat sealed layers of honey-dosed foam/fiber, super absorbent material, non-woven material, the bacterial barrier layer, and casting layer, and the liner layer; placing dressing pouch layers substantially over and under the cut, heat sealed layers of honey-dosed foam/fiber, super absorbent material, non-woven material, the bacterial barrier layer, and the casting layer and the liner layer; heating the dressing pouch layers to substantially join the dressing pouch layers together, thereby enclosing the cut, heat sealed layers of honey-dosed foam/fiber, super absorbent material, non-woven material, the bacterial barrier layer, and the casting liner and the liner layer together; and cutting the heat sealed, dressing pouch layers enclosing the super absorbent, honey-dosed foam/fiber composite, gap patterned wound dressing to form individual super absorbent, honey-dosed foam/fiber composite wound dressings.

In an embodiment of the third aspect of the present invention, the step of placing a layer of super absorbent material substantially over a layer of foam/fiber material includes the step of utilizing a super absorbent panel as the super absorbent material.

The preferred super absorbent, honey-dosed or impregnated, gap patterned foam/fiber wound dressing, according to various embodiments of the present invention, offers the following advantages: ease of use; improved dressing strength; reduced dressing weight; increased efficiency and controlled lay down of honey; increased ability to deliver an equal measure of honey across the wound bed; increased ability to promote controlled, naturally occurring osmotic delivery action of the honey onto the wound bed; increased rate of absorption of exudates while allowing honey stored within the honey-dosed or impregnated area to flow naturally onto the wound; improved ease of handling of the dressing; intelligent management of exudates through the foam/fiber composite into the super absorbent panel; the honey is dispersed faster and more evenly into the wound; dressing liners allow for easy handling of the dressing and protect the dressing from accidental damage; improved odor control; and the single-sided application of honey to dressing presents the honey dose to the wound face of dressing rather than wasting unused honey on the bandage side of dressing. In fact, in many of the preferred embodiments, these factors of improved strength, reduced weight, increased lay down efficiency, increased honey loading, increased honey delivery, increased osmotic delivery action, increased exudate absorption ability, improved ease of handling, intelligent management of exudates, honey dispersion, the use of dressing liners, improved odor control, and the single-sided application of honey to the dressing are optimized to an extent that is considerably higher than heretofore achieved in prior, known honey-based wound dressings.

BRIEF DESCRIPTION OF DRAWINGS

The above mentioned features and steps of the invention and the manner of attaining them will become apparent, and the invention itself will be best understood by reference to the following description of the embodiments of the invention in conjunction with the accompanying drawings, wherein like characters represent like parts throughout the several views and in which:

FIG. 15A is a perspective view of an adherent honey-dosed, foam/fiber composite dressing having super absorbency covered with a protective liner, constructed according to the present invention;

FIG. 15B is a further perspective view of the adherent honey-dosed, foam/fiber composite dressing of FIG. 15A with the protective liners partially removed;

FIG. 23 is an exploded, side view of the adherent honey-dosed, foam/fiber composite dressing of FIGS. 15A and 15B;

FIG. 24 is an exploded, side view of another adherent honey-dosed foam/fiber composite dressing, which is constructed according to the present invention;

FIG. 26 is an exploded, side view of an adherent honey impregnated, gauze composite dressing, which is constructed according to the present invention;

FIG. 27 is an exploded, side view of another adherent honey impregnated, gauze composite dressing, which is constructed according to the present invention;

DETAILED DESCRIPTION OF PREFERRED EMBODIMENTS

Figure 1:
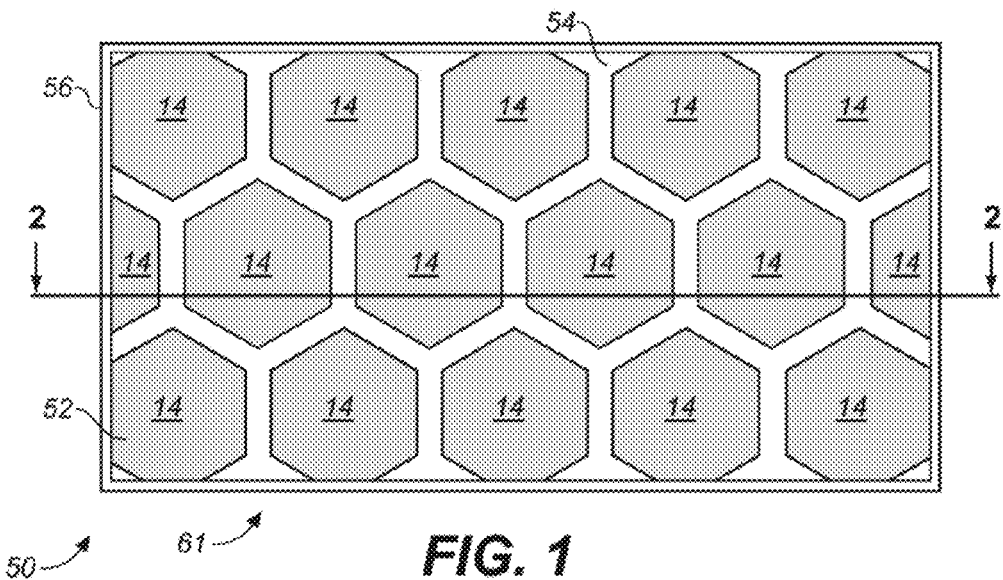
FIG. 1 is a top view of a gap-patterned medical grade foam dressing, constructed according to the present invention.
Figure 2:
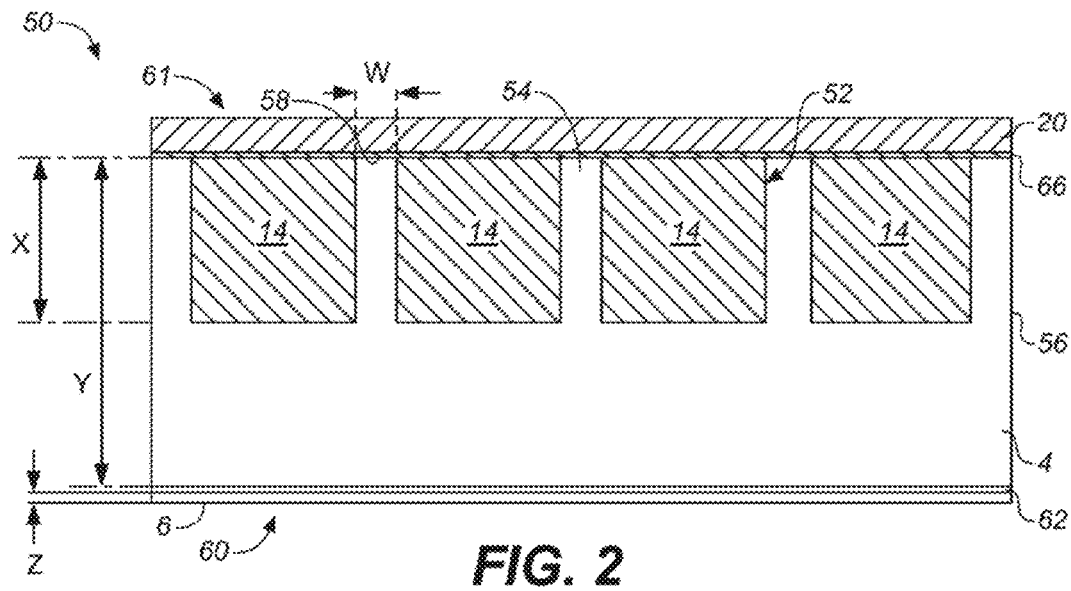
FIG. 2 is a cross-sectional view of the gap-patterned medical grade foam dressing taken substantially along line 2-2 of FIG. 1.
Figure 3:
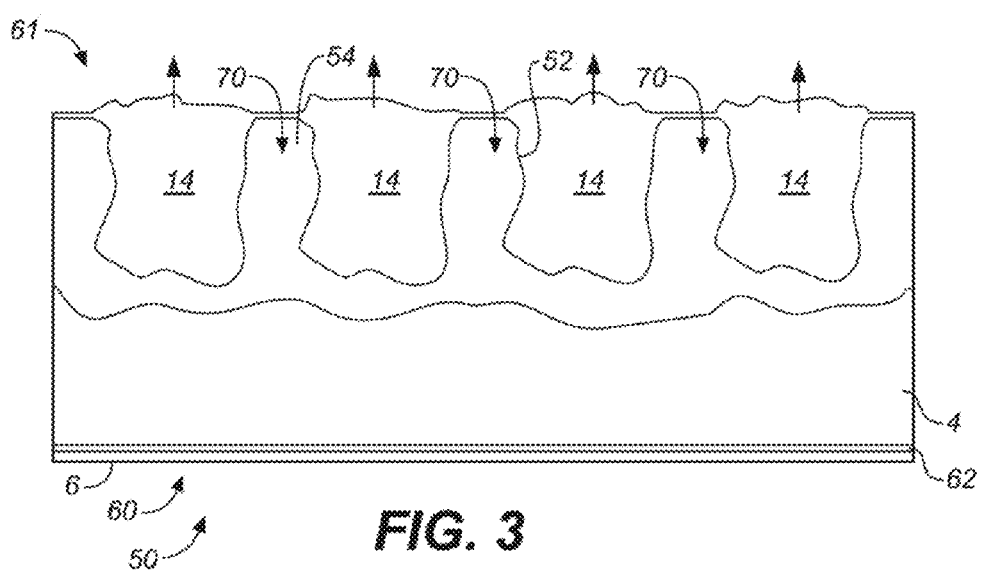
FIG. 3 is a diagrammatic illustration of a gap-patterned medical grade foam dressing, wherein an exudate has caused the foam gap patterned areas to swell and expand thereby dispersing the honey out of the honey deposits in the foam.

Referring now to the drawings and more particularly to FIGS. 1-3, there is illustrated a gap-patterned medical grade foam dressing 50, which is constructed in accordance with the present invention. As will be explained hereinafter in greater detail, the dressing 50 is constructed to provide a pumping action that pulls or draws exudates from a wound into the dressing 50 and disperses a precise dose of honey 14 from the dressing 50 throughout the wound treatment zone. The advantages of foam dressing 50 are the improved management of exudates through the foam gap patterned areas in dressing 50, the swelling of the foam gap patterned areas supports natural osmotic pump action of the honey, tackiness in dressing 50 is reduced because there are gaps between the honey-dosed areas, the honey is dispersed faster and more evenly into the wound, dry edges around dressing 50 allow for easy handling of the dressing 50 and protect the dressing from accidental damage, and the single-sided application of honey to dressing 50 presents the honey dose to the wound face of dressing 50 rather than wasting unused honey on the bandage side of dressing 50.

Considering now the gap-patterned medical grade foam dressing 50, in greater detail with reference to FIGS. 1-3, the gap-patterned medical grade foam dressing 50 generally includes a flexible sheet of polyether polyurethane foam 4 having a non-wound contact side indicated generally at 60 (FIG. 2) and a wound contact side indicated generally at 61 (FIG. 2). The non-wound side 60 of the dressing 50 is protected with a breathable barrier 6, having a (Z) thickness of about 30 microns, as best seen in FIG. 2. The barrier 6 is composed of a sheet of breathable polyurethane. While barrier 6 is cosmetic, its purpose is to protect the dressing 50 from debris and liquid contamination.

Dressing 50 may also be provided with a dry picture frame edge 56 (FIGS. 1 and 2) which facilitates ease of handling of the dressing 50 during the wound dressing application process. Foam 4 is medical grade foam that is highly absorbent, flexible, porous and fully breathable to help facilitate the formation of a moist wound environment which is highly conducive for body healing purposes.

As best seen in FIG. 2, the wound contact side 61 of the dressing 50 is provided with a patterned plurality of foam gaps 54 interspersed with a patterned plurality of honey-dosed foam areas 52. The foam gaps 54 are formed in the foam 4 when the foam 4 is dosed with honey 14, which is an important feature of the present invention. That is, the patterns of honey-dosed foam areas 52 and the patterns of non-dosed foam gaps 54 cooperate with one another to create a pumping, push-pull action that allows the dressing 50 to: 1) absorb or pull wound exudates from a treated wound area into the non-dosed foam gaps 54; and 2) to disperse substantially the totality of the honey 14 in the honey-dosed foam areas 52 onto the treated wound area covered by the dressing 50.

While in the preferred embodiment of the present invention, the patterned dressing 50 is illustrated as being provided with a gapped honeycomb pattern, it should be appreciated by those skilled in the art, that any suitable gap-patterned shape can be employed, although the gapped hexagon pattern is the preferred shape. Studies on the geometry of the honeycomb pattern explain that no other shape can create more space. Circles for instance leave spaces, and squares make smaller areas. In addition, the hexagon structure reduces the weight of dressing 50.

Furthermore, the honeycomb design allows for the most efficient and controlled lay down of honey 14 onto the dressing 50, creating roughly 300 honey-dosed areas 52 in a 10×10 cm dressing. It is calculated that each honey-dosed area 52 will contain around 0.025 g of honey 14. The gap-patterned foam matrix also allows for the dressing 50 to remain flexible and pliable making it easily conformable to the wound.

With respect to foam 4, foam 4 preferably is constructed of any suitable medical grade, breathable, absorbent, flexible and porous polymeric foam, preferably, medical grade polyether polyurethane foam. It is to be understood that the foam should create a moist wound environment which triggers the bodys natural healing ability. Finally, foam 4 should be sufficiently absorbent to hold deposits of honey 14 in place but not so absorbent as to allow the deposits of honey 14 to run into the non-dosed foam walls or foam gaps 54 disposed between the honey deposits.

As shown more clearly in FIG. 2, foam 4 should have a thickness in a range (Y) of between 0.1 mm minimum to about a maximum of 25 mm, with a preferable thickness of approximately 4 mm.

Also as shown more clearly in FIG. 2, the non-dosed foam walls or gaps 54 of patterned foam dressing 50 should have a thickness in a range (W) of between 0.05 mm minimum to about a maximum of 100 mm, with a preferable thickness of 1 mm. It is to be understood that the thickness (W) should be of a range which allows sufficient absorption and swelling, while also maintaining the cosmetic look and separation of honey-dosed areas 52 within the gap-patterned foam dressing 50.

With respect to the honey 14 utilized to dose the foam 4, medical grade Manuka, Pasture, Ling Kahami, Portobello, Greek Pine, Yorkshire, Chilean Ulmo, Chilean Rain Forrest, Australian Eucalyptus, Himalayan, Scottish Heather, Scottish Wild Flower, English Heather, English Wildflower, New Zealand Clover, Australian Clover, Cuban Comparitan, Acacia, Spanish Blossom, Tasmanian Leatherwood, Organic Honey All, New Zealand Beach, Kanuka, New Zealand Bush, New Zealand Honey Dew, Jarrah, Thyme, and Kamahi honeys are all known to contain superior anti-bacterial and anti-inflammatory factors and thus are preferred honeys for the dressing 50. Manuka honey also has the ability to have a rapid deodorizing effect with patients having malodorous fumigating wounds, which could be due to the inhibition of anaerobic bacterial growth. Finally, the high sugar levels in honey may well result in osmotic pressure that promotes autolytic debridement and, for these reasons, Manuka honey is the preferred honey for use in the dressing 50. The high sugar levels in the honey result in osmotic pressure that promotes autolytic debridement. The terminology "osmotic pressure" is defined herein to mean the pressure required to maintain equilibrium of two solutions, with no net movement between one solution (e.g., a solvent) and the other solution. The terminology "autolytic debridement" is defined herein to mean a process by which the body's own enzymes and moisture is used to re-hydrate, soften and liquefy hard eschar and slough (i.e., dry scab and dead tissue.

As shown in FIG. 2, the gap-patterned foam dressing 50 has a dosed honey depth in a range (X) which is between approximately a minimum of 0.1 mm to about a maximum of 24.9 mm, with a preferred dose depth of about 3 mm.

Regarding the dosage of honey 14 in dressing 50, the ratio of honey weight to total weight of dressing 50 will vary depending upon the size and style of dressing 50. Preferably, the depth of the patterned foam dressing 50 is sufficient to hold a specific amount of honey 14 of between 50%-75% of honey 14 to the total weight of dressing 50. Also, it is to be understood that the target dose of honey 14 for a 4 inch by 4 inch (10 cm×10 cm) dressing 50 is between 0.5 g to 100 g, with the preferable dosage being 8-10 g. However, it is to be understood that balance is critical in that overdosing dressing 50 with honey 14 may result in a functional failure of dressing 50 because the foam structure 4 may become over saturated thereby decreasing the rate at which dressing 50 absorbs exudates. It is to be understood that it is not necessary to have a three-dimensional shape with a flat bottom. The bottom could taper off into a point.

The majority of the honey 14 is contained within the dosed areas 52 but the surface of the dressing 50 has a micro thin or minimal trace layer 58 of honey 14, which is of such a minimal amount that the top surface is not sticky and is easy to handle. Moreover, the dressing 50 has been designed with dry edges 56 (FIGS. 1 and 2) around all four sides of dressing 50, thereby reducing tackiness of dressing 50. This allows for easy handling relative to placing dressing 50 on a wound once the protective liner 20 (FIG. 2) has been removed and the dressing face is exposed. It is to be understood that tackiness of dressing 50 is reduced because there are gaps between the honey-dosed areas. The dosing is controlled, thus not saturating the dressing 50. The honey 14 is dosed into the areas 52 thus creating optimal storage of the honey 14 within the honey-dosed areas 52. It is to be further understood that dry edges 56 can allow extra capacity for quick ingress of exudates on higher exuding wounds. Finally, it is to be understood that dressing 50 may not include dry edges 56. It is to be understood that honey 14 is prevented from oozing off of dry edges 56 because the moisture within honey 14 is reduced once it is dosed into the foam 4.

As shown more clearly in FIGS. 2-3, foam walls or gaps 54 are designed to absorb exudates from the wound down through and into the areas between honey-dosed areas 52 at the rear of the dressing 50. In this manner, areas 52 disperse the honey 14 throughout the wound treatment zone through the naturally occurring osmotic action. This design allows for an even delivery of honey 14 across the wound bed.

With respect to FIG. 2, barrier 6, preferably, is any suitable, breathable barrier constructed of polyurethane film. While barrier 6 is cosmetic, the purposes of barrier 6 are to provide a barrier to stop bacterial infection from outside of the wound, to stop any honey 14 from potentially bleeding through barrier 6, to protect the dressing 50 from debris or liquid contamination and to stop exudates from bleeding through dressing 50. Preferably, the thickness (Z) of barrier 6 is around 30 microns. Barrier 6 is preferably, conventionally pre-coated with a medical grade medium tack acrylic or silicone pressure sensitive adhesive 62. It is to be understood that barrier 6 can also be attached to gap-patterned dressing 50 by conventional heat bonding.

Located over honey 14 in patterned dressing 50 is a conventional, peelable liner 20 which is attached to patterned dressing 50 by thin micro or minimal trace layer 58 of honey 14.

As shown more clearly in FIG. 3, an important feature of the patterned dressing 50 is the foam walls or gaps 54 between the honey-dosed areas 52. The foam walls or gaps 54 in the patterned dressing 50 permit exudates 70 (water) to pass through and between the honey-dosed areas 52 and collect in foam walls or gaps 54. This enhances a naturally occurring osmotic pumping action by causing the foam walls or gaps 54 to swell, thereby taking up space and applying pressure to the honey-dosed areas 52. As can be seen in FIG. 3, exudates 70 cause foam walls or gaps 54 to expand out which, in turn, applies pressure to the adjacent honey-dosed areas 52. As a result, the honey 14 is dispersed out of honey-dosed areas 52. This provides a steady supply of honey 14 throughout the wound treatment zone. This action will continue until the honey 14 is depleted which results in substantially the complete dispersion of the honey 14 from the dressing 50 throughout the wound treatment zone.

Figure 4:
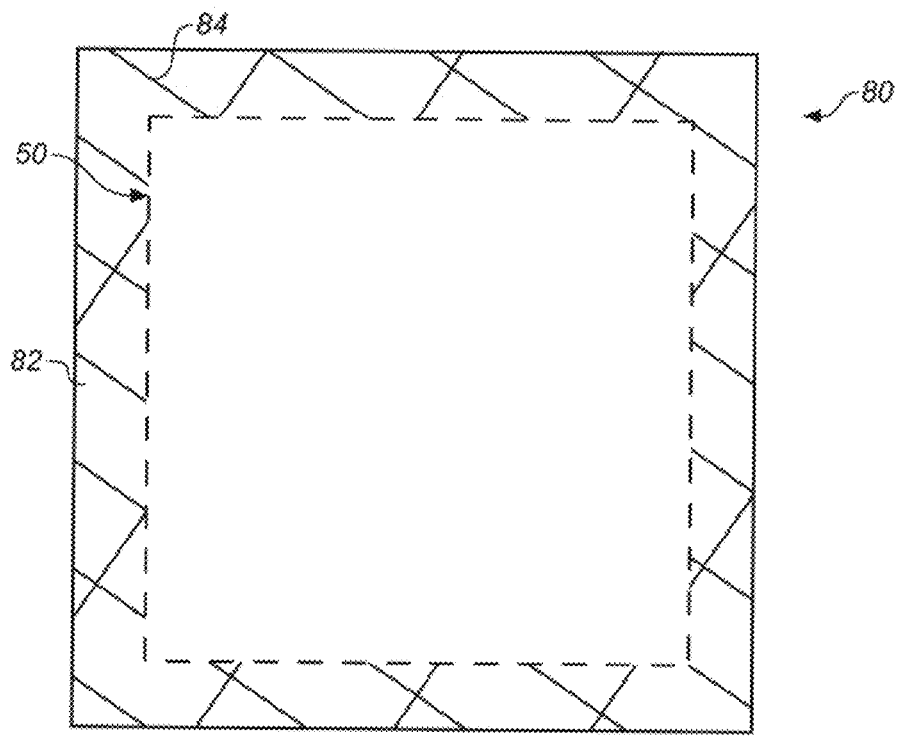
FIG. 4 is a schematic illustration of a pouch which contains a sterile, gap-patterned medical grade foam dressing, constructed according to the present invention.

With respect to FIG. 4, there is illustrated a complete dressing package 80 that includes a pouch 82 which encloses a gap-patterned, medical grade foam dressing 50. Pouch 82, preferably, is constructed of any suitable polyester and/or polyethylene material so as to provide a moisture barrier for dressing 50. Located around the perimeter of pouch 82 is a conventional, peelable adhesive 84 which allows the pouch 82 to be easily opened to remove dressing 50 but at the same time provides adequate moisture barrier properties to protect dressing 50.

The following EXAMPLE is being provided in order to more clearly disclose the inventive concepts of the present invention.

Example

Foam is cut in order to form a 4 inch by 5 inch (10 cm by 12.5 cm) base for the dressing. Approximately, 8-11 grams of honey are dosed into a pattern of honey-dosed areas and foam walls or gaps on the dressing base to form the dressing. The total weight of dressing (honey and foam structure) was determined to be 17 grams. After the dressing has been prepared, it is packed into a pouch 80 (FIG. 4) and conventionally passed through a gamma irradiation plant, which is validated to FDA & ISO standards. The gamma rays irradiate and kill any live pathogens that are present in any type of particulate or other form.

Experiment

In order to prove the efficacy of the present invention the following experimental results are provided.

The purpose of the experiment is to establish the absorption rate of medical foam dressings dosed with honey. To compare the relative absorption rates between continuous surface dosed dressings with selective gap-pattern dosed dressings where areas of the foam surface are free from honey.

Apparatus
a. Samples of foam cut to 4×4 cm
b. Straight sided metal ring with 35 mm internal diameter
c. Water
d. Measuring Cylinder
e. Timer
f. Clean Flat Plate Method
g. Place dressing sample on to flat clean plate.
h. Place one open end of metal ring onto the dressing sample.
i. Measure 10 ml of water using a pipette or other suitable device.
j. Dispense contents of measuring device into the metal ring on the dressing.
k. Time how long it takes for the water to be fully absorbed into the dressing.
l. If the timing is difficult to adequately establish the absorption rate, use more or less water.
m. Thoroughly clean and dry the apparatus between each test.
n. Use the same amount of water for each test.

Results
o. Table I below shows the results obtained with a cross section of different samples:
p.

TABLE I

| Dressing Type | Time in Seconds | | | | | | |
|---|---|---|---|---|---|---|---|
| | Test 1 | Test 2 | Test 3 | Test 4 | Test 5 | Test 6 | Average |
| Plain Control | 6.83 | 6.20 | 6.89 | 7.72 | | | 6.91 |
| 1.5 mm wall thickness | 9.98 | 8.29 | 9.24 | | | | 9.17 |
| 1.25 mm wall thickness | 8.56 | 11.21 | 8.57 | 8.96 | 7.66 | 8.34 | 8.88 |
| 1 mm wall thickness | 11.12 | 11.86 | 10.30 | | | | 11.09 |
| 0.75 mm wall thickness | 14.79 | 11.49 | 13.09 | 15.29 | | | 13.67 |
| 0.5 mm wall thickness | 11.04 | 12.39 | 10.65 | 12.90 | | | 11.75 |
| Fully coated | 20.95 | 28.51 | 64.28 | 36.78 | 40.51 | 37.57 | 38.10 |

CONCLUSIONS q. It appears from the above results that there is an increase in absorption rate where there are gaps between the honey deposits. This could be because the gaps provide a free channel for fluids to access the storage capacity of the foam.
r. Probably the presence of honey taking up capacity in the dressing, which would otherwise be available for absorption of fluids, has a proportional impact on the rate of absorption. This was suggested by the fact that the heavier dosed samples more quickly became saturated, with the excess fluid bleeding through the dressing and onto the plate around. This fluid had honey dispersed in it.

s. The 0.75 mm and 0.5 mm wall thickness samples were not completely clear of honey between the deposits, so the results appear to be skewed slightly.

Figure 14:
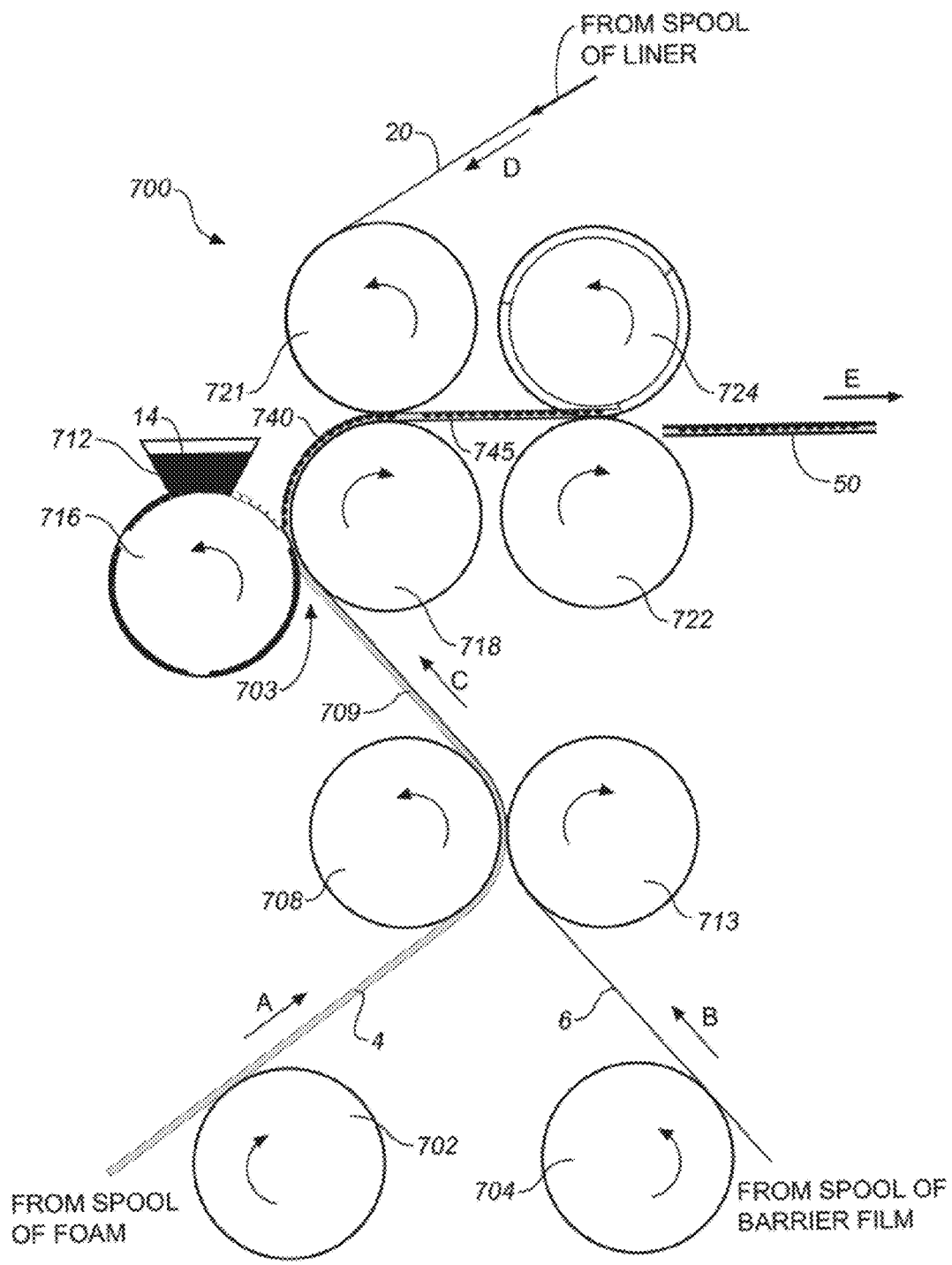
FIG. 14 is a schematic illustration of the construction of a gap-patterned medical grade foam dressing, constructed according to the present invention.

Referring back to the drawings and more particularly to FIG. 14, a dressing construction apparatus 700 is illustrated, which apparatus 700 is constructed in accordance with the present invention. The apparatus 700 forms ribbons of foam dressing which are cut to a predetermined length and then packaged by means not shown for shipping purposes. In this regard, the results provide individual packages, such as a package 80 for containing the foam dressing 50.

Considering now the method of constructing the foam dressing 54 in greater detail, the apparatus 700 generally includes a first set of feed rollers indicated at 702 and 704, respectively. Feed roller 702 pulls into a construction path (A) a ribbon of foam 4 from a spool of foam (not shown). The ribbon of foam 4 has a width dimension required for the dressing 50. Feed roller 704 pulls into another construction path (B), a ribbon of barrier 6, whose width dimension corresponds to the width dimension of the ribbon of foam 4. The A construction path and the B construction path merge at the nip of a pair of laminating rollers 708 and 713, respectively. In this regard, the foam 4 and barrier 6 traverse along the direction of the construction paths A and B, respectively wherein the foam 4 and the barrier 6 are laminated together between the conventional laminating rollers 708 and 713 to create lamination 709. The laminating rollers 708 and 713 then cooperate with a pair of upstream rollers, namely a heated form roller 716 and a drive roller 718.

The heated form roller 716 is in fluid contact with a reservoir 712 of liquid honey 14 so when the surface of roller 716 passes by the reservoir 712, the conventionally heated roller 716 withdraws a predetermined amount of honey 14 from reservoir 712. It is to be understood that reservoir 712 can be located at other positions in apparatus 700. The honey coated roller 716 and drive roller 718 then engage the lamination 709 at their nip 703 which doses the foam side of lamination 709 such that a pattern of honey-dosed foam areas and a pattern of gap foam areas or walls are created in foam 4. A thin micro or minimal trace layer (58 in FIG. 2) of honey is deposited on the surface of the patterned surface of the patterned dosed foam 740 as it emerges from between rollers 716 and 718, respectively.

As the gap-patterned foam 740 emerges from between the heated form roller 716 and drive roller 718, it is further pulled upstream by a feed roller 721 which helps drive a liner 20 into a nip between the drive roller 718 and the feed roller 721 so that liner 20 is applied to the wet surface of the gap-patterned foam 740 to form a liner covered gap-patterned foam ribbon, indicated generally at 745. In this manner, liner 20 is retained on gap-patterned foam 740 by honey micro or minimal trace layer 58 (FIG. 2).

Next, ribbon 745 is pulled upstream by a drive roller 722 and a conventional rotary tool roller 724 which cooperate for die cutting the liner covered gap-patterned foam ribbon 745 as ribbon 745 passes between rollers 722 and roller 724, where it emerges as the dressing 50. It is to be understood that all rollers, as mentioned herein, turn at substantially the same surface speed as lamination 709, which can be anywhere between 1 m/minute and 15 m/minute. As mentioned previously, the dressing 50 then passes into a packaging mechanism (not shown) which packages individual ones of the dressing 50 in a pouch 80 package for ease of handling and radiation.

Although the preferred method of dosing foam with honey 14 to create or form a gap-patterned foam dressing 50 is illustrated by the apparatus 700 (FIG. 14), it is contemplated that honey 14 may be placed within honey-dosed areas 52 of dressing 50 by other types of apparatus for depositing honey, including but not limited to coating, dosing, pasting, impregnating, injecting, pouring, spraying, transferring, printing (all methods) including lithography, stencilling, flexography, gravure, infusion, and rotogravure. It is to be understood that a honey coating (not shown) maybe conventionally imprinted upon foam dressing 50 so that it appears to be a gap-patterned structure dosed with honey 14

Figure 5:
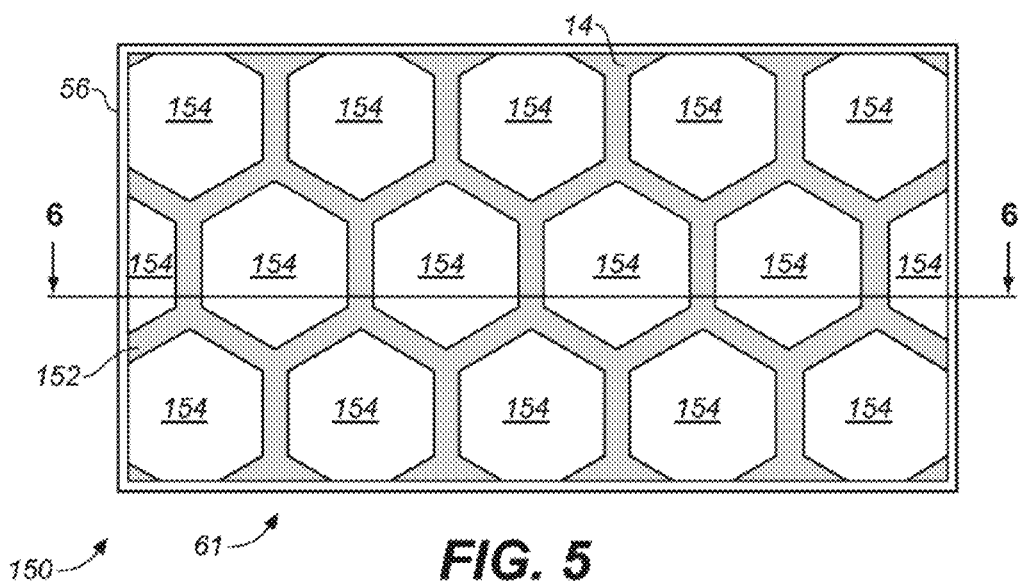
FIG. 5 is a top view of another gap-patterned foam dressing, constructed according to the present invention.
Figure 6:
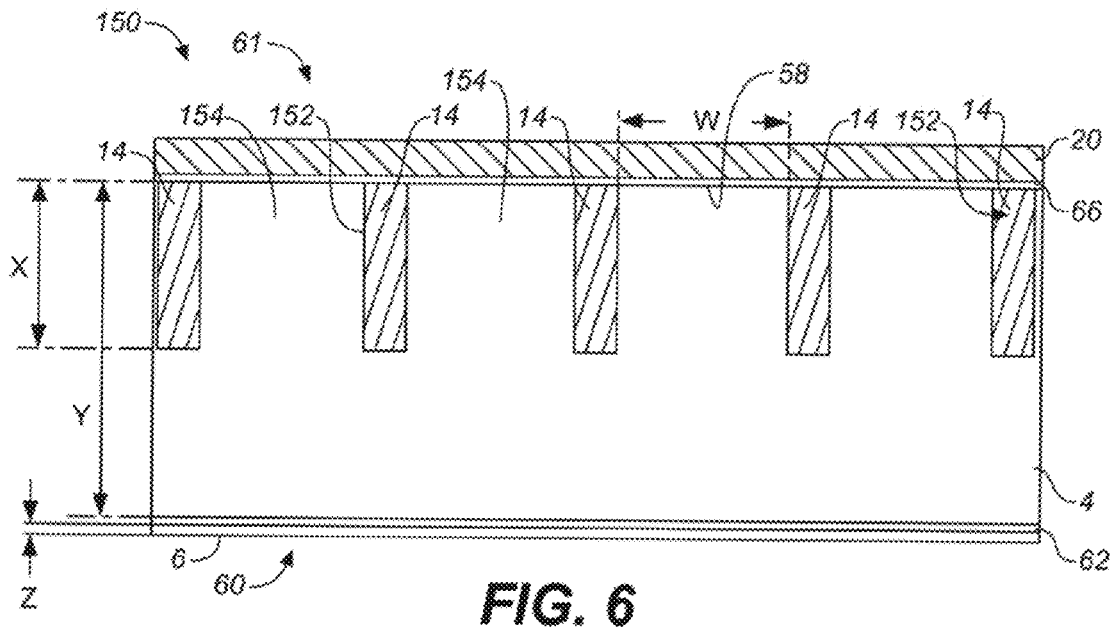
FIG. 6 is a cross-sectional view of the gap-patterned medical grade foam dressing of FIG. 5, taken substantially along line 6-6 of FIG. 5.
Figure 7:
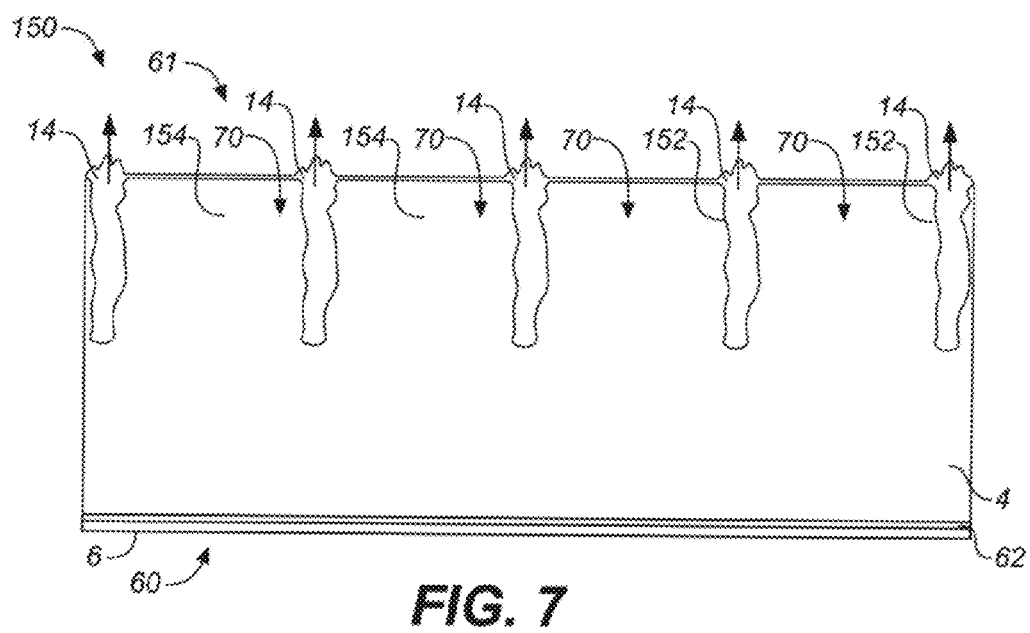
FIG. 7 is a diagrammatic illustration of a gap-patterned medical grade foam dressing, wherein an exudate has caused the foam gap patterned areas to swell and expand thereby dispersing the honey out of the honey deposits in the foam.

Referring now to the drawings and more particularly to FIGS. 5-7 there is shown another gap-patterned medical grade foam dressing 150, which is constructed, in accordance with the present invention. The gap-patterned foam dressing 150 is the reverse of foam dressing 50. That is, the dressing 150 is provided with non-honey-dosed gaps 154 having a hexagon shape such that non-honey-dosed hexagon shaped gaps 154 are interspersed with honey-dosed areas 152. Other than the patterned shapes as mentioned herein, the foam dressing 150 is substantially similar to foam dressing 50. Since foam dressings 50 and 150 are similar, it will suffice to mention that the foam dressing 150 is provided with a smaller dose of honey 14 since the honey 14 is dosed into smaller areas 152 than those of dosed area 52 in the dressing 50. Honey by weight in this embodiment therefore is 25-50% by weight as opposed to between 50-75% by weight. Also like dressing 50, dressing 150 is provided with a micro thin or minimal trace layer 58 of honey 14 on its upper surface which is also covered with a protective cover 20, just as was the case with dressing 50. The bottom surface of the foam 4 is further covered with a breathable barrier 6 which is adhered to the foam 4 by an adhesive 62, just as was the case with dressing 50.

As shown more clearly in FIG. 7, an important feature of the patterned dressing 150 is the foam walls or gaps 154 between the honey-dosed areas 152. The foam walls or gaps 154 in the patterned dressing 150 permit exudates 70 (water) to pass through and between the honey-dosed areas 152 and collect in foam walls or gaps 154. This enhances a naturally occurring osmotic pumping action by causing the foam walls or gaps 154 to swell, thereby taking up space and applying pressure to the honey-dosed areas 152. As can be seen in FIG. 7, exudates 70 cause foam walls or gaps 154 to expand out which, in turn, applies pressure to the adjacent honey-dosed areas 152. As a result, the honey 14 is dispersed out of honey-dosed areas 152. This provides a steady supply of honey 14 onto the wound treatment zone. This action will continue until the honey 14 is dispersed inside and outside the dressing 150. As discussed earlier, the foam walls or gaps 154 of patterned foam dressing 150 should have a thickness in a range of between 0.05 mm minimum to about a maximum of 100 mm, with a preferable thickness of 4 mm.

Figure 8:
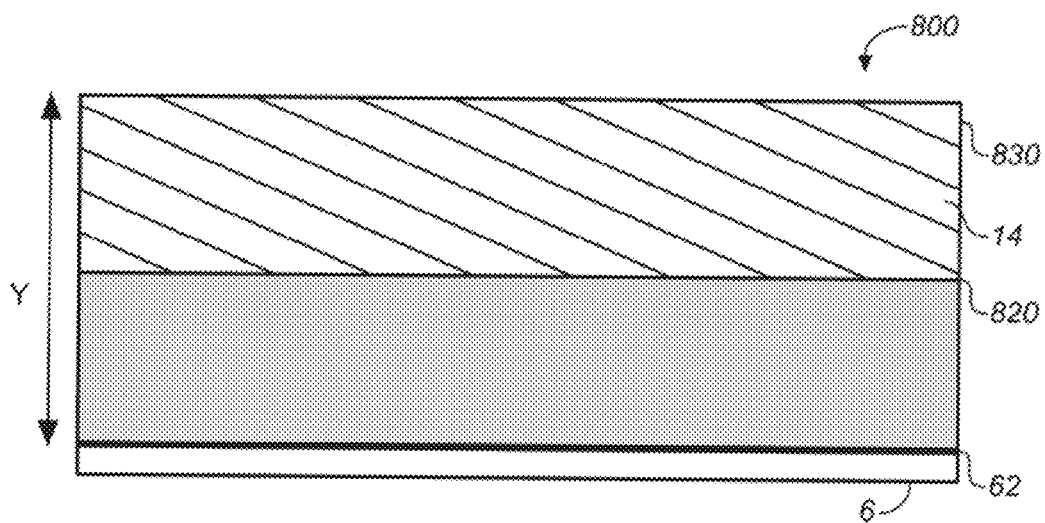
FIG. 8 is a diagrammatic illustration of another medical grade foam dressing, constructed according to the present invention.

Referring now to the drawings and more particularly to FIG. 8, there is shown a honey-dosed foam dressing 800, which is constructed in accordance with the present invention. Use of foam dressing 800 offers several advantages. For example, air passing through the foam regulates moisture levels at the wound site to further promote healing. Also, micro-holes in the foam act as air filters to keep debris and particulates out of the wound while simultaneously letting fresh air into the wound. Foam dressing 800 is substantially waterproof and quickly dries-out after getting wet. Also, the foam is flexible and stays in place when the body is in motion. In addition, the foam material is resilient, such that the foam material moves with the skin. This resiliency prevents the foam material from tearing and separating from the wound site due to skin movement. Also, thicker foam dressings provide cushioning that make inadvertent contact or impact with the wound site less painful.

As described in more detail herein below, honey-dosed foam dressing 800 comprises a substrate 820 made of an absorbent foam material. The foam material 820 has a predetermined weight and thickness. Honey 14 is layered on one side of the foam substrate 820. Honey 14 has a predetermined weight as a percentage of the total weight of dressing 800. As with dressings 50 and 150, honey-dosed foam dressing 800 is used as a wound dressing, wherein the honey layer contacts the wound site to promote healing of the wound when the dressing is applied.

The specific embodiment of the honey-dosed foam dressing 800 will now be described. In this regard, and with reference to FIG. 8, honey-closed foam dressing 800 is a wound dressing comprising one or two components combined into a single unit. One component is a foam substrate 820. A second component is a fiber reinforcement 822 to provide stability to the foam substrate. The uncompressed density of foam substrate 820 is between 95-150 kg/m$^3$. Foam substrate 820 is, preferably, about 3-4 mm thick. Foam 820, preferably, is constructed of medical grade plastic polymer foam, such as polyether polyurethane foam.

Foam substrate 820 should have a thickness in a range (Y) of between 0.1 mm minimum to about a maximum of 25 mm, with a preferable thickness of approximately 4 mm.

With respect to FIG. 8, barrier 6, preferably is any suitable, breathable barrier constructed of polyurethane which is conventionally pre-coated with a medical grade medium tack acrylic or silicone pressure sensitive adhesive 62. While barrier 6 is cosmetic, the purposes of barrier 6 are to provide a barrier to stop bacterial infection from outside of the wound, to stop any honey 14 from potentially bleeding through barrier 6, to protect the dressing 800 from debris or liquid contamination and to stop exudates from bleeding through dressing 800. Preferably, the thickness of barrier 6 is around 30 microns. It is to be understood that barrier 6 can also be attached to gap-patterned dressing 800 by conventional heat bonding.

Another component is honey 14 disposed on one side of foam substrate 820, so that a honey layer 830 is created by an even disposition of honey 14 throughout foam substrate 820. Honey layer 839 is preferably less than about 75% by weight of the total weight of wound dressing 800. As with wound dressings 50 and 150, foam wound dressing 800 is applied such that honey layer 830 contacts the wound site to promote healing of the wound.

Figure 9:
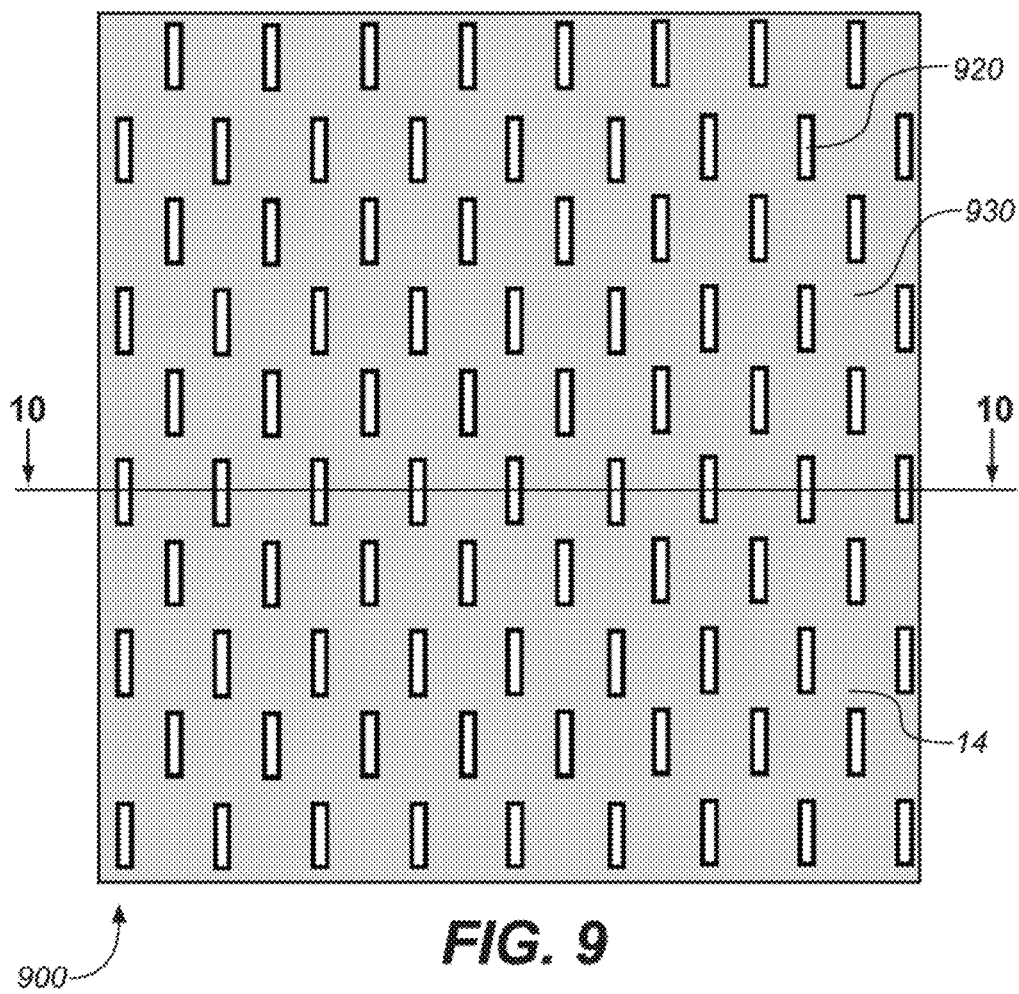
FIG. 9 is a top view of a medical grade gauze dressing with gaps in the structure of the gauze and an anti-tackiness protective layer on both sides, which is constructed in accordance with the present invention.
Figure 10:
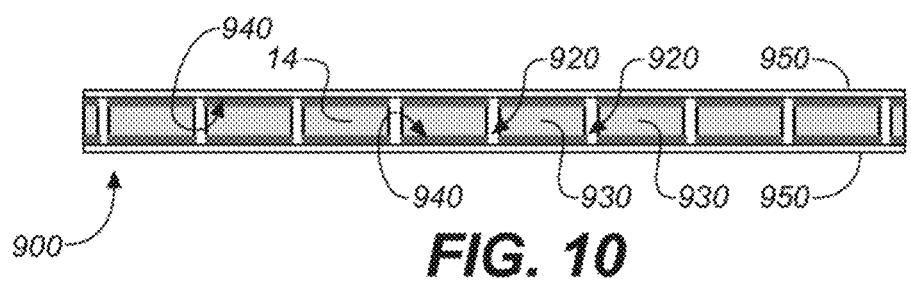
FIG. 10 is a cross-sectional view of the medical grade gauze dressing taken substantially along line 10-10 of FIG. 9.

Referring now to the drawings and more particularly to FIGS. 9-10, there is shown a honey-dosed gauze dressing 900, which is constructed in accordance with the present invention. As described in more detail herein below, honey-dosed gauze dressing 900 comprises a material, such as gauze, which contains gaps in the gauze. The surface of the gauze is dosed with honey, such that the honey resides within the gauze between the gaps but substantially not in the gaps. As with dressings 50, 150 and 800, the side of the material containing the honey is placed on the wound to promote healing of the wound. An anti-tackiness coating, sheet or protective layer may or may not cover the honey.

Honey comb gauze dressing 900 exhibits several advantages. As stated herein above, the gauze contains the honey within its structure. This particular structure of the gauze holds more honey than standard honey-dosed gauze dressings. The gaps in the gauze allow for greater expansion, conformity and flexibility of the dressing. Furthermore, the gaps allow for the free passage of exudate, if present, within the wound, so that this may be more quickly collected and managed by any absorbent materials surrounding the wound treatment zone. Also, in one embodiment, honey-dosed gauze dressing 900 includes an anti-tackiness coating, sheet or protective layer covering the honey for reducing the risk that the dressing will undesirably adhere to the wound site and will provide the gauze with an anti-tackiness feeling to touch. However, the structure of the honey-dosed gauze dressing 900 can advantageously eliminate the need for an anti-tackiness layer covering the honey and therefore, in another embodiment, the anti-tackiness layer is omitted. Finally, as previously discussed herein, the high sugar levels found in the honey, result in an osmotic pressure that promotes autolytic debridement.

Referring back to FIG. 9, honey comb gauze dressing 900 will now be described. In this regard, and with reference to FIG. 9, honey comb gauze dressing 900 includes a pattern of gaps 920 and surrounding fabric 930. Gauze dressing 900, preferably, has a weight of approximately 300 grams per meter squared.

Gauze dressing 900 is woven, knitted or structured so as to define a plurality of laterally adjacent linear shaped gaps 920 therein, illustrated with white background, as best seen in FIG. 9. Gaps 920 form a regular pattern similar to the parallel walls between the cells on a honey comb, in this manner, honey-dosed gauze dressing 900 forms a matrix that may be considered analogous to the structure of a bee's honey comb.

Honey 14 is disposed into gauze dressing 900 in the fabric 930 to completely fill the structure around the gaps 920. For clarity of understanding the gauze dressing 900, the honey 14 is shown in FIGS. 9-10 as unobstructed shaded areas. The honey dose 14 is used, among other things, to reduce the risk of wound infection and to promote healing, as with dressings 50, 150 and 800. The preferred weight of honey dose for this presentation is between 65-70% of the total dressing weight.

Located on either side of gauze dressing 900 is an anti-tackiness coating, sheet or layer 940 and an additional protective cover 950 over honey-dosed fabric 930. Anti-tackiness coating, sheet or layer 940 will reduce the risk that dressing 900 will undesirably adhere to the wound site. In this regard, anti-tackiness layer 940 should have a low stickiness property (i.e., low ability to retain solvents upon drying). Such an anti-tackiness layer 940 may comprise silicone oil, embossed or un-embossed polymer liners or other suitable anti-tackiness compositions. As shown in FIG. 9, anti-tackiness layer 940 may be on either or both sides of gauze dressing 900 and contacts the wound when honey-dosed dressing 900 is applied.

Figure 11:
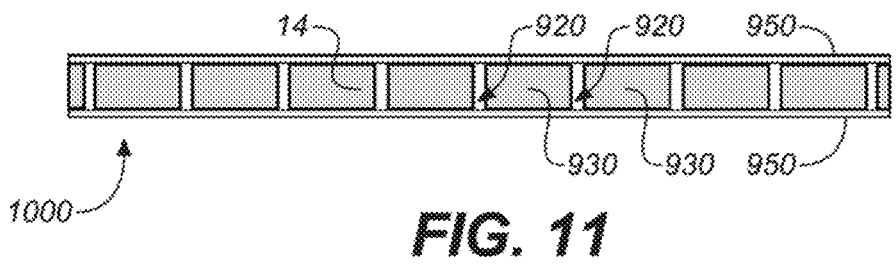
FIG. 11 is a diagrammatic illustration of the medical grade gauze dressing of FIG. 10 with the anti-tackiness layer removed.

Referring now to the drawings and more particularly to FIG. 11, a honey-dosed gauze dressing 1000 is illustrated. The honey-dosed gauze dressing 1000 is substantially similar to honey-dosed gauze dressing 900 except, however, the structure of honey-dosed gauze dressing 1000 allows for the elimination of anti-tackiness layer 940 (FIG. 9), if desired. The ability to eliminate the anti-tackiness layer 940 without affecting the functionality of honey-dosed gauze dressing 1000 is due to the surface texture of the honey-dosed gauze dressing 1000. It is also to be understood that the elimination of anti-tackiness layer 940 in honey-dosed gauze dressing 1000 may also reduce the amount of material comprising the dressing and, therefore, may reduce manufacturing costs.

Figure 12:
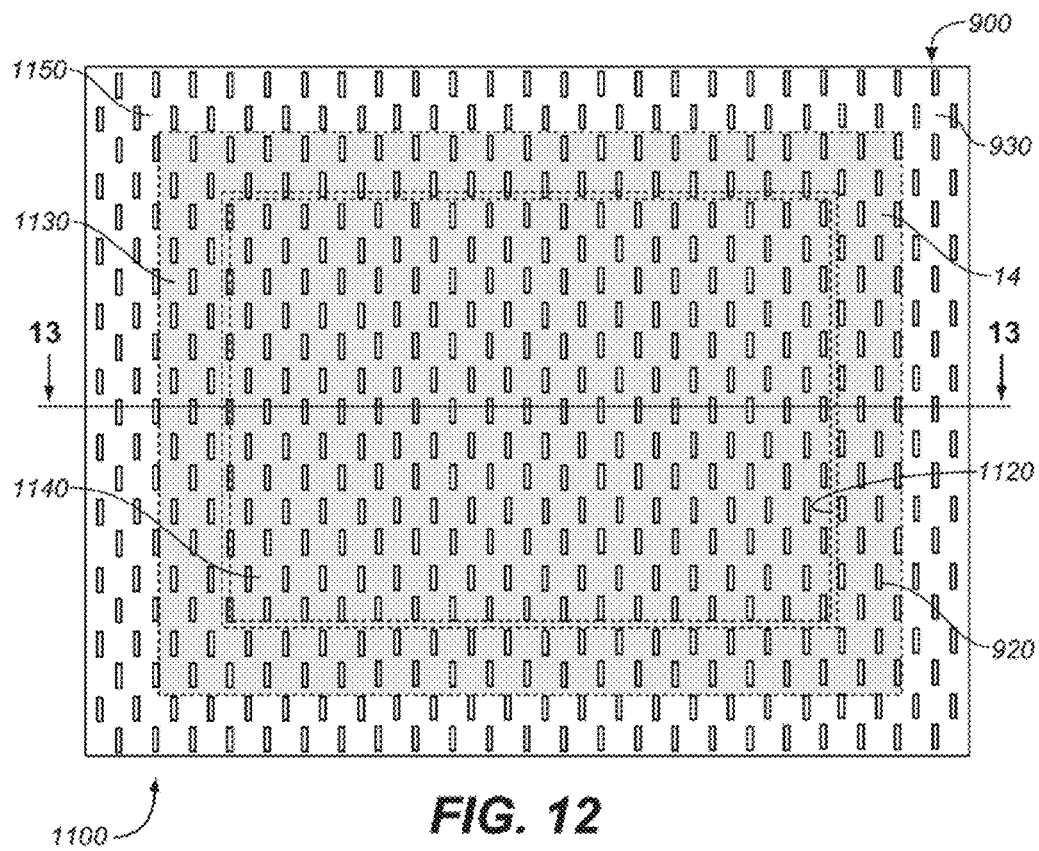
FIG. 12 is a diagrammatic illustration of a medical grade gauze dressing including a pouch in which an absorbent pad is located, which is constructed in accordance with the present invention.
Figure 13:
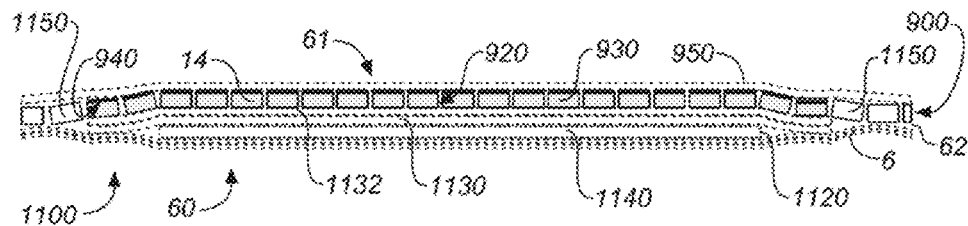
FIG. 13 is a cross-sectional view of the medical grade gauze dressing taken substantially along line 13-13 of FIG. 12.

Referring now to the drawings and more particularly to FIGS. 12-13, there is shown a honey-dosed gauze dressing 1100, which is constructed in accordance with the present invention. As described in more detail herein below, honey-dosed gauze dressing 1100, having a non-wound contact side indicated generally at 60 (FIG. 13) and a wound contact side indicated generally at 61 (FIG. 13), comprises a material, such as gauze, which contains gaps in the gauze, in combination with an absorbent pad located in a pouch attached to the gauze. The surface of the gauze is dosed with honey, such that the honey resides within the gauze around the gaps. As with dressings 50, 150, 800, 900 and 1000, the side of the material containing the honey is placed on the wound to promote healing of the wound. An anti-tackiness coating, sheet or protective layer may or may not cover the honey.

Honey-dosed gauze dressing 1100 exhibits several advantages. As stated herein above, the gauze contains the honey within its structure. The gaps in the gauze allow for greater conformity and flexibility of the dressing. Furthermore, the gaps allow for the free passage of exudate from the wound, so that this can be collected and managed by the absorbent pad located within the pouch underneath the honey-dosed gauze. The absorbent pad contains super absorbent powder to manage high levels of exudate, locking it within the secure pouch. The choice of the material for the wicking layer which forms one side of the pouch, between the honey-dosed gauze and the absorbent pad, allows a slow initial transfer of exudate which thereby reduces the risk of painful wound treatment often associated with the application of super absorbent dressings. Maintaining a steady rate of transfer of exudate promotes the complete dispersal of honey throughout the wound treatment zone. Also, honey-dosed gauze dressing 1100 includes a protective cover and a picture frame dry edge for ease of handling during application (FIG. 13). Finally, as previously discussed herein, the high sugar levels found in the honey, result in an osmotic pressure that promotes autolytic debridement.

Referring back to FIGS. 12-13, honey-dosed gauze dressing 1100 will now be described. In this regard, and with reference to FIG. 13, honey-dosed gauze dressing 1100 includes the same gauze described in dressing 900 above. A pouch 1120 is formed from an adhesive coated wicking layer 1130 and the polyurethane barrier 6, as described more fully for dressing 50, which forms the backing to dressing 1100. Inside the pouch 1120, an absorbent pad 1140 is located to collect and manage exudate from the wound. The wicking layer 1130 has an acrylate or thermal adhesive 1132 which has the necessary wet performance properties to regulate the flow of exudate through the dressing.

Gauze 900 is woven, knitted or structured so as to define a plurality of laterally adjacent linear shaped gaps 920 therein, illustrated with white background, as best seen in FIG. 9. Gaps 920 form a regular pattern similar to the parallel walls between the cells on a honey comb. In this manner, honey-dosed gauze dressing 900 forms a matrix that may be considered analogous to the structure of a bee's honey comb.

Honey 14 is disposed into gauze 900 in the fabric 930 to completely fill the structure apart from the gaps and the picture frame dry edge feature shown more clearly in FIG. 12. For clarity of understanding the gauze dressing 1100, the honey 14 is shown in FIG. 12 as unobstructed shaded areas. The honey dose 14 is used, among other things, to reduce the risk of wound infection and to promote healing, as with dressings 50, 150, 800, 900 and 1000. The preferred weight of honey dose for this presentation is between 45-65% of the total dressing weight. Finally, it is to be understood that dressing 1100 may not include dry edges 1150.

Located on the wound contact face 61 of dressing 1100 is an anti-tackiness coating, sheet or layer 940 and an additional protective cover 950 over honey-dosed fabric 930. Anti-tackiness coating, sheet or layer 940 will reduce the risk that dressing 1100 will undesirably adhere to the wound site. In this regard, anti-tackiness layer 940 should have a low stickiness property (i.e., low ability to retain solvents upon drying). Such an anti-tackiness layer 940 may comprise silicone oil, or other suitable anti-tackiness compositions. It is to be understood that, as described above for dressing 1000, the anti-tackiness layer 940 may not be included in dressing 1100 which will reduce manufacturing costs, without affecting the functionality of dressing 1100, due to the surface texture of the gauze 900. Referring now to the drawings and more particularly to FIGS. 15A and 15B, there is illustrated an, adherent, super absorbent, honey-dosed composite dressing 1500, which is constructed in accordance with the present invention. As will be explained hereinafter in greater detail, the adherent, super absorbent, honey-dosed composite dressing 1500 is constructed to dispense a precise dose of honey to a wound treatment area while pulling or drawing exudates from the wound treatment area. The advantages of the adherent, super absorbent, honey-dosed composite dressing 1500 are increased ability to promote controlled, naturally occurring osmotic delivery action of honey into a wound bed, increased rate of absorption of exudates while allowing honey stored within the honey-dosed areas of the dressing to flow naturally onto the wound, the intelligent management of exudates through a foam/fiber composite construction and into a super absorbency material, ease of use and handling, improved dressing strength, reduced dressing weight, increased efficiency and the controlled lay down of honey into a wound area.

Figure 15C:
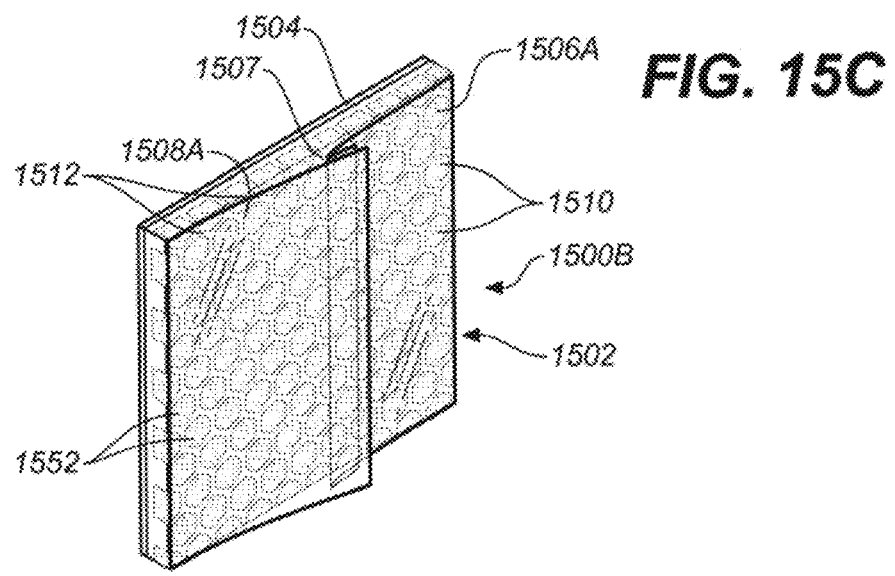
FIG. 15C is a perspective view of the placement of the protective, removable liners over a non-adherent super absorbent honey-dosed, foam/fiber composite dressing having super absorbency.
Figure 15D:
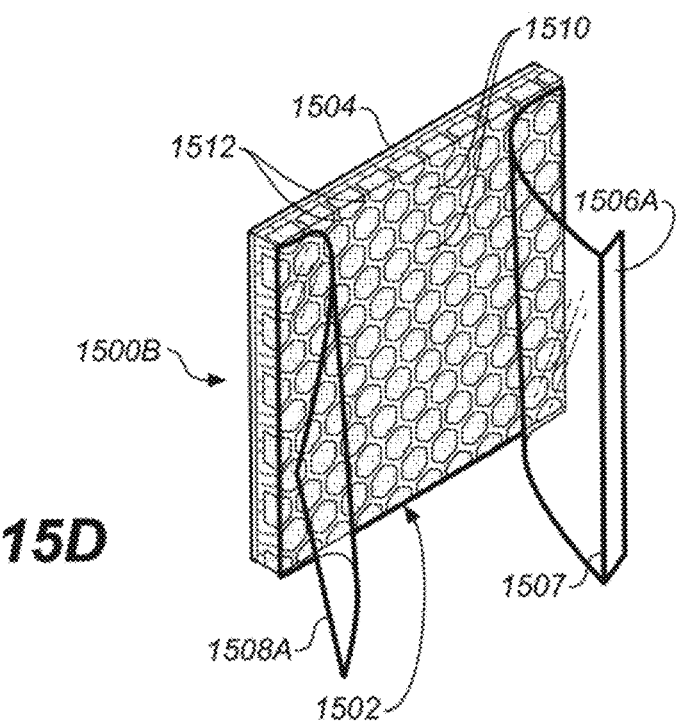
FIG. 15D is a perspective view of the non-adherent super absorbent honey-dosed, foam/fiber composite dressing of FIG. 15C with the protective liners partially removed.
Figure 16A:
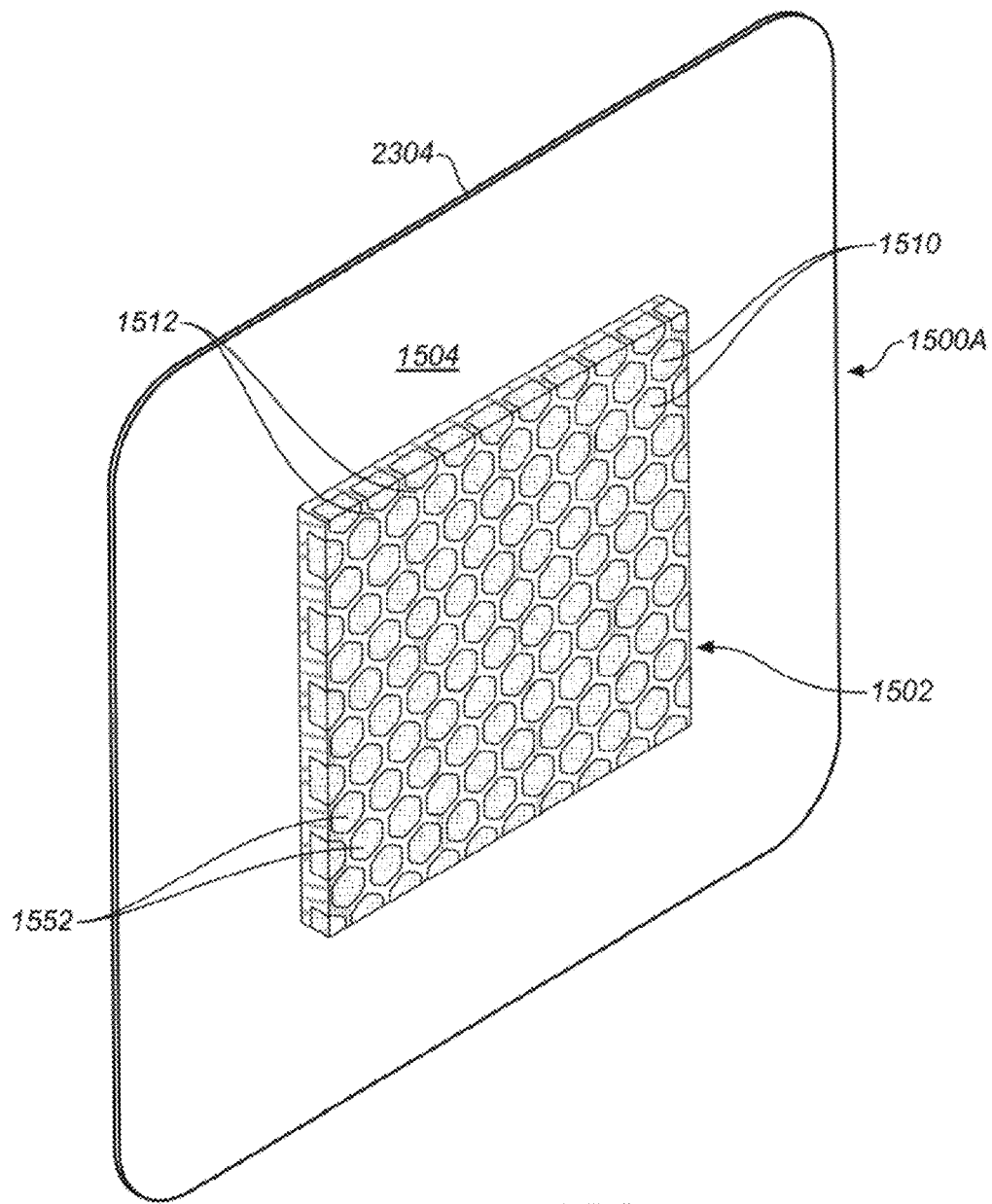
FIG. 16A is a still yet a further perspective view of an adherent honey-dosed foam/fiber composite dressing of FIGS. 15A and 15B, with the protective removable liners being completely removed.
Figure 16B:
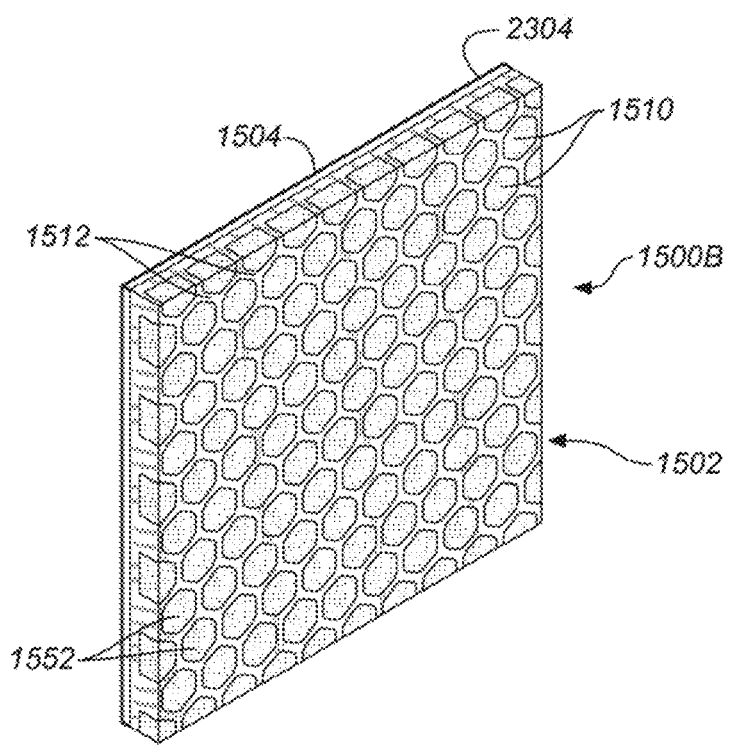
FIG. 16B is a still yet a further perspective view of a non-adherent, honey-dosed, foam/fiber composite dressing of FIGS. 15C and 15D, with the protective liners being completely removed.

Considering now the super absorbent, honey-dosed composite dressing 1500 in greater detail, the super absorbent, honey-dosed composite dressing 1500 generally includes a foam/fiber composite construction 1502 and a bacterial barrier layer 1504. In order to protect the super absorbent, honey-dosed composite dressing 1500 from accidental exposure prior to being applied to a wound treatment area, such as wound treatment area 2704, as best seem in FIG. 29, the super absorbent, honey-dosed composite dressing 1500 is also provided with a pair of protective removable liners, such as a protective removable liner 1506 and a protective removable liner 1508. Depending upon the size of the bacterial barrier layer 1504 relative to the foam/fiber composite construction 1502, the protective removable liners 1506 and 1508 are sized to protect either both the foam/fiber composite construction 1502 and the bacterial barrier layer 1504, as best seen in FIGS. 15A and 15B to provide an adherent composite dressing 1500A (FIG. 16A), or, in the alternative, to protect only the foam/fiber composite construction 1502 as best seen in FIGS. 15C and 15D to provide a non-adherent composite dressing 1500B (FIG. 16B). In this later case, the protective removable liners are identified as a protective removable liner 1506A and a protective removable liner 1508A to distinguish their smaller size relative to the protective removable liners 1506 and 1508, respectively.

Figure 29:
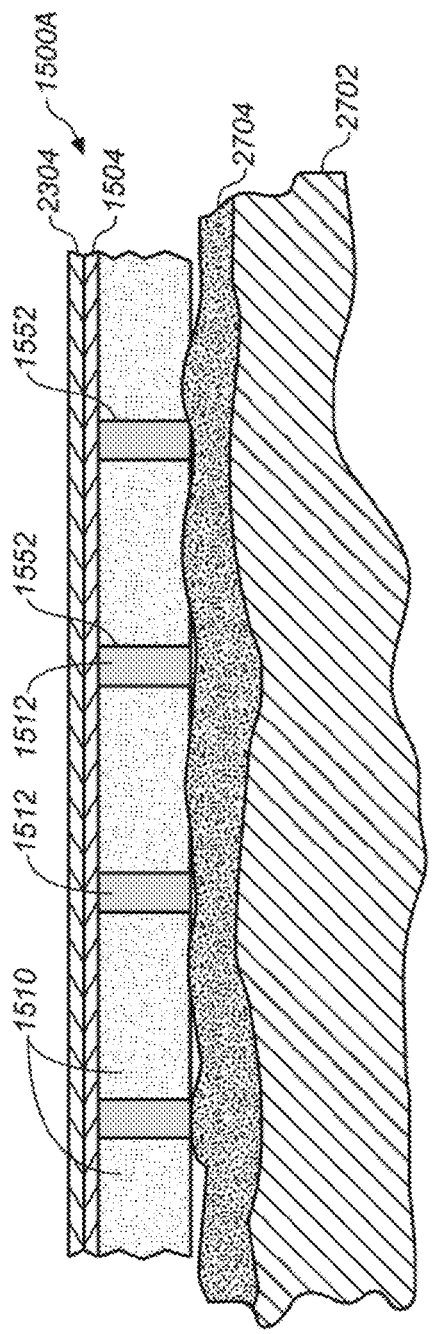
FIG. 29 is a schematic illustration of the honey-dosed foam/fiber composite dressing of FIG. 16A, being applied to a wound, according to the present invention.

Considering now the bacterial barrier layer 1504 in greater detail, the bacterial barrier layer 1504 preferably, is constructed of any suitable medical grade, breathable polyurethane. The bacterial barrier layer 1504 is provided with a non-wound facing side and a wound facing side. The non-wound facing side is provided with a removable casting liner 2304 which acts as a fluid stop preventing any exudates absorbed by the foam/fiber composite construction 1502 from leaking out the backside of the adherent composite dressing 1500A. The wound facing side of the bacterial barrier layer 1504 is coated with a skin compatible adhesive 1504A, as best seen in FIG. 23, to enable the bacterial barrier layer 1504 to be secured to a non-wound facing surface of the foam/fiber composite construction 1502 and to the removable protective liners 1506 and 1508, respectively, in the case of the adherent composite wound dressing 1500A. The skin compatible adhesive 1504A also enables the adherent dressing 1500A to be secured to the patient at wound area, such wound area 2704 (FIG. 29).

Considering now the protective removable liners 1506 and 1508 respectively, only liners 1506 and 1508 will be described hereinafter in greater detail as protective removable liners 1506A and 1508A are constructed substantially the same except for size. Removable liners 1506 and 1508, preferably, are constructed of medical grade polyethylene. Also, a fold 1507 is conventionally created along one edge of removable liner 1506 to aid in the removal of liners 1506 and 1508.

FIG. 5A illustrates the placement of the protective removable liners 1506 and 1508 over a wound facing surface area of the composite dressing 1500. In FIG. 15B, the protective removable liners 1506 and 1508 are being conventionally, partially peeled away from the super absorbent, honey-dosed composite dressing 1500 in order to expose the foam/fiber composite construction 1502 so as to facilitate the application of super absorbent, honey-dosed composite dressing 1500 to a wound treatment area, such as wound area 2704 (FIG. 29). FIG. 16A illustrates the honey-dosed foam/fiber composite adherent dressing 1500A where the protective removable liners are completely removed from the composite dressing 1500.

In use, the super absorbent, honey-dosed composite dressing 1500 is easy to handle as the honey bearing, foam/fiber composite construction 1502 is protected from accidental and unwanted exposure by the protective liners 1506 and 1508. As best seen in FIGS. 15A, 15B, and 16A, as the liners 1506 and 1508 are peeled away and completely removed, the foam/fiber composite construction 1502 is completely exposed thereby providing a ready to use adherent dressing 1500A (FIG. 16A) which may be directly applied to a wound treatment area 2704, as best seen in FIG. 29.

As best seen in FIGS. 15A and 15B, the foam/fiber composite construction 1502, the bacterial barrier layer 1504, and removable liners 1506 and 1508 are generally rectangular in shape. It should be understood however, by those skilled in the art, that the foam/fiber composite construction 1502, the bacterial barrier layer 1504, and removable liners 1506 and 1508 may be provided in other shapes and, in this regard, their shapes are not limited to rectangular shapes as described herein.

In the case of the non-adherent composite wound dressing 1500B (FIG. 16B), the wound facing side of the bacterial barrier layer 1504 is secured only to the non-wound facing surface of the foam/fiber composite construction 1502. As will be described in greater detail later with respect to FIGS. 15A, 15B, 16A, 16B and 23-28, the bacterial barrier layer 1504 and the removable liners 1506 and 1508 may be constructed to have a surface area size which is substantially greater than the surface area size of the foam/fiber composite construction 1502 to provide the adherent, super absorbent, honey-dosed composite dressing 1500A, as best seen in FIG. 16A, or in the alternative, the bacterial barrier layer 1504 and the removable liners 1506A and 1508A may be constructed to have a surface area size which substantially conforms to the surface area size of only the foam/fiber composite construction 1502 to provide the non-adherent, super absorbent, honey-dosed composite dressing 1500B, as best seen in FIG. 16B.

FIG. 15C illustrates the placement of the protective, removable liners 1506A and 1508A over a wound facing surface area of the foam/fiber composite construction 1502. In FIG. 15D, the protective removable liners 1506A and 1508A are being conventionally partially peeled away from the non-adherent, super absorbent, honey-dosed composite dressing 1500B in order to expose the foam/fiber composite construction 1502 so as to facilitate the application of the non-adherent, super absorbent, honey-dosed composite dressing 1500B to a wound treatment area, such as wound area 2704 (FIG. 29).

In use, as best seen in FIGS. 15C and 15D, as the liners 1506A and 1508A are peeled away and completely removed, the foam/fiber composite construction 1502 is completely exposed thereby providing a ready to use non-adherent, super absorbent, honey-dosed composite dressing 1500B (FIG. 16B) which may be directly applied to a wound treatment area, such as wound area 2704 (FIG. 29).

As best seen in FIGS. 15C and 15D, the foam/fiber composite construction 1502, the bacterial barrier layer 1504, and the removable liners 1506A and 1508A are generally rectangular in shape. It should be understood however, by those skilled in the art, that the foam/fiber composite construction 1502, the bacterial barrier layer 1504, and the removable liners 1506A and 1508A may be provided in other shapes and, in this regard, their shapes are not limited to rectangular shapes, as described herein.

Figure 17:
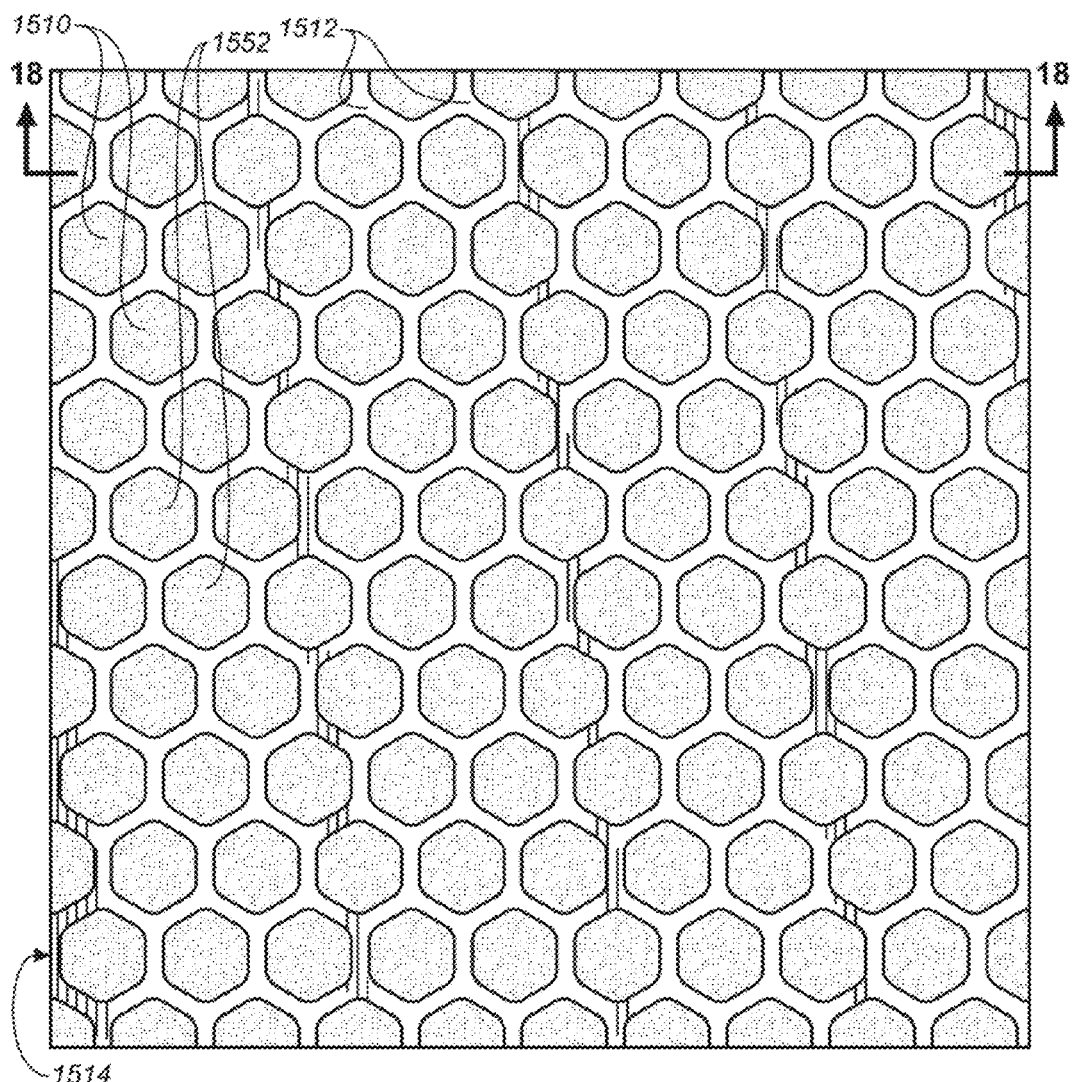
FIG. 17 is a top view of a honey-dosed, foam/fiber composite construction, forming part of the adherent honey-dosed foam/fiber composite dressing of FIG. 16A and the non-adherent honey-dosed foam/fiber composite dressing of FIG. 16B.
Figure 18:
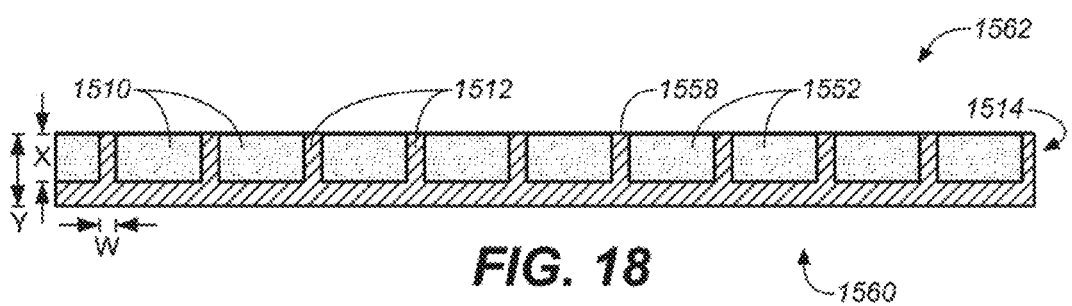
FIG. 18 is a cross-sectional view of the honey-dosed, foam/fiber composite construction, taken substantially along line 18-18 of FIG. 17.
Figure 21:
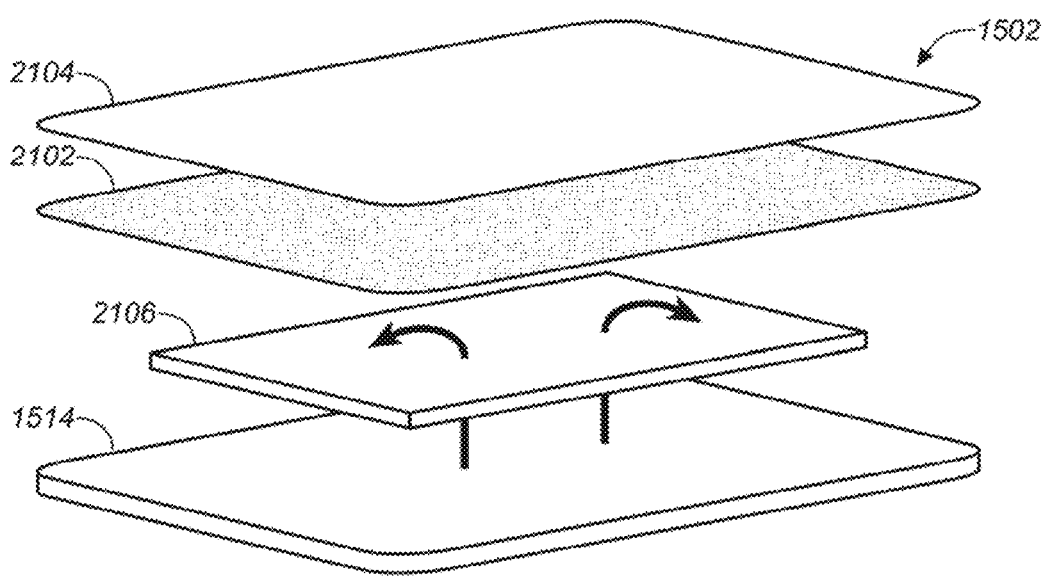
FIG. 21 is a schematic, exploded, perspective view of a honey-dosed, foam/fiber composite, forming part of the adherent honey-dosed, foam/fiber composite dressing of FIGS. 15A, 15B, and 16A and the non-adherent honey-dosed, foam/fiber composite dressing of FIGS. 15C, 15D, and 16B.

Considering now the foam/fiber composite construction 1502 in greater detail with reference to FIG. 21, the foam/fiber composite construction 1502 generally includes a non-woven fabric layer 2104, a super absorbent panel layer 2106, and an open cell, honey-dosed, foam/fiber structure 1514 which is capable of being dosed or impregnated by honey, generally indicated at 1510, as best seen in FIGS. 17 and 18. Preferably, the non-woven fabric layer 2104 is a medical-grade, non-woven material which has a discontinuous hot-melt thermal adhesive coating 2102 conventionally applied to one face. As will be described hereinafter in greater detail, heat is applied by physical pressure of an electrically heated tool within a construction process of manufacturing. This creates a thermal bond between the layers (2104, 2106, and 1514) of the super absorbent, honey-dosed, foam/fiber composite construction 1502.

A unique aspect of the non-woven fabric layer 2104 is its wicking capabilities. Non-woven fabric layer 2104 causes exudate to be continuously fed from the wound to the super absorbent panel layer 2106 (rather than a speed related function, which could be seen as causing discomfort to the patient). Preferably, non-woven fabric layer 2104 is 100 mm×100 mm.

Super absorbent panel layer 2106, preferably, is constructed of a conventional medical-grade, super absorbent polymer. The capacity of the super absorbent polymer, preferably, is 4700%/© (e.g. 150 g/sq.m dry super absorbent panel (SAP) to absorb 7050 g/sq.m fluid). Preferably, super absorbent panel layer 2106 is constructed in shapes ranging in size from 70 mm×70 mm to 80 mm×80 mm, depending upon the application. The weight of super absorbent panel layer 2106, preferably, is about 0.735 g on a 10 cm×10 cm dressing. Ideally, super absorbent panel 2106 will assist in drawing exudates away from foam/fiber structure 1514 so that foam/fiber structure 1514 does not become saturated with exudates. In this manner, super absorbent panel 2106 allows foam/fiber structure 1514 to remain very efficient in removing exudates from the wound area of the patient while allowing foam/fiber structure 1514 to continue to provide honey to the wound area 2704 (FIG. 29).

Preferably, the foam/fiber structure 1514 is constructed of medical grade polyether polyurethane foam with a polyolefin (non-absorbent) fiber matrix to create structural stability in the foam/fiber structure 1514. Preferably, the foam/fiber structure 1514 is generally rectangular in shape with a preferred size of about 100 mm×100 mm. The foam/fiber structure 1514 has a thickness in the range Y, as best seen in FIG. 18, of between about a minimum of 0.1 mm to a maximum of about 25.0 mm, with a preferable thickness of approximately 4.0 mm.

When dosed or impregnated with honey, a gap-patterned structure is formed where honey is dosed into the foam/fiber structure 1514 in a honeycomb design pattern of honeycomb structures separated by gaps as best seen in FIGS. 17-18. Honey 1510 is dosed to a depth of about X mm, where X is between approximately a minimum of 0.1 mm to about a maximum of 24.9 mm, with a preferred dose depth of about 3.0 mm. As described above, the honeycomb design allows for the most efficient and controlled lay down of honey 1510 onto the foam/fiber structure 1514, creating roughly 300 honey-dosed or impregnated areas 1552 in a 10×10 cm foam/fiber structure 1514. It is calculated that each honey-dosed or impregnated area 1552 will contain around 0.025 g of honey 1510. The gap-patterned matrix also allows for the foam/fiber structure 1514 to remain flexible and pliable making it easily conformable to the wound.

With respect to the honey 1510 utilized to impregnate or dose the foam/fiber structure 1514, as described above, medical grade Manuka, Pasture, Ling Kahami, Portobello, Greek Pine, Yorkshire, Chilean Ulmo, Chilean Rain Forrest, Australian Eucalyptus, Himalayan, Scottish Heather, Scottish Wild Flower, English Heather, English Wildflower, New Zealand Clover, Australian Clover, Cuban Comparitan, Acacia, Spanish Blossom, Tasmanian Leatherwood, Organic Honey All, New Zealand Beach, Kanuka, New Zealand Bush, New Zealand Honey Dew, Jarrah, Thyme, Australian Jelly Bush, Leptospermum based honey and Kamahi honeys are all known to contain superior anti-bacterial and anti-inflammatory factors and thus are preferred honeys for the foam/fiber structure 1514. Manuka honey also has the ability to have a rapid deodorizing effect with patients having malodorous fumigating wounds, which could be due to the inhibition of anaerobic bacterial growth. Finally, the high sugar levels in honey may well result in osmotic pressure that promotes autolytic debridement and, for these reasons, Manuka honey is the preferred honey for use in the foam/fiber structure 1514. The high sugar levels in the honey result in osmotic pressure that promotes autolytic debridement. The terminology "osmotic pressure" is defined herein to mean the pressure required to maintain equilibrium of two solutions, with no net movement between one solution (e.g., a solvent) and the other solution. The terminology "autolytic debridement" is defined herein to mean a process by which the body's own enzymes and moisture is used to re-hydrate, soften and liquefy hard eschar and slough (i.e., dry scab and dead tissue).

As discussed above, the amount of honey 1510 in foam/fiber structure 1514 and the ratio of honey weight to total weight of foam/fiber structure 1514 will vary depending upon the size and style of foam/fiber structure 1514. Preferably, the depth of the gap pattern in foam/fiber structure 1514 is sufficient to hold a specific amount of honey 1510 of between 50%-75% of honey 1510 to the total weight of foam/fiber structure 1514. Also, it is to be understood that the target amount of honey 1510 for a 4 inch by 4 inch (10 cm×10 cm) foam/fiber structure 1514 is between 0.5 g to 100 g, with the preferable amount being 8-10 g. However, it is to be understood that balance is critical in that overdosing foam/fiber structure 1514 with honey 1510 may result in a functional failure of foam/fiber structure 1514 because the foam/fiber structure 1514 may become over saturated thereby decreasing the rate at which foam/fiber structure 1514 absorbs exudates.

The majority of the honey 1510 is contained within the dosed or impregnated areas 1552 (FIGS. 17 and 18) but the surface of the foam/fiber structure 1514 has a micro thin or minimal trace layer 1558 of honey 1510, which is of such a minimal amount that the top surface is not sticky and is easy to handle. It is to be understood that tackiness of foam/fiber structure 1514 is reduced because there are gaps 1512 between the honey-dosed or impregnated areas 1552. The dosing is controlled, thus not saturating the foam/fiber structure 1514. The honey 1510 is dosed into the areas 1552 thus creating optimal storage of the honey 1510 within the honey-dosed areas 1552.

It is to be understood that honey 1510 is prevented from oozing off of the edges of foam/fiber structure 1514 because the moisture within honey 1510 is reduced once it is dosed into the foam/fiber structure 1514.

Considering now the honey comb patterned, foam/fiber structure 1514, in greater detail with reference to FIGS. 17 and 18, the honey comb patterned, foam/fiber structure 1514 generally includes a non-wound contact side indicated generally at 1560 (FIG. 18) and a wound contact side indicated generally at 1562 (FIG. 18). As best seen in FIG. 18, the wound contact side 1562 of the foam/fiber structure 1514 is provided with a patterned plurality of gaps 1512 interspersed with a patterned plurality of honey-dosed or impregnated areas 1552. The gaps 1512 are formed in the foam/fiber structure 1514 when the foam/fiber structure 1514 is dosed or impregnated with honey 1510, which is an important feature of the present invention. That is, the patterns of honey-dosed or impregnated areas 1552 and the patterns of non-dosed or impregnated gaps 1512 cooperate with one another to create a pumping, push-pull action that allows the foam/fiber structure 1514 to: 1) absorb or pull wound exudates from a treated wound area into the non-dosed or impregnated gaps 1512; and 2) to disperse substantially the totality of the honey 1510 in the honey-dosed or impregnated areas 1552 onto the treated wound area covered by the foam/fiber structure 1514.

Also, as shown more clearly in FIG. 18, the non-dosed or impregnated walls or gaps 1512 of honey-dosed, foam/fiber structure 1514 should have a thickness in a range (W) of between 0.05 mm minimum to about a maximum of 100 mm, with a preferable thickness of 1 mm. It is to be understood that the thickness (W) should be of a range which allows sufficient absorption and swelling, while also maintaining the cosmetic look and separation of honey-dosed or impregnated areas 1552 within the honey-dosed or impregnated foam/fiber structure 514.

Figure 19:
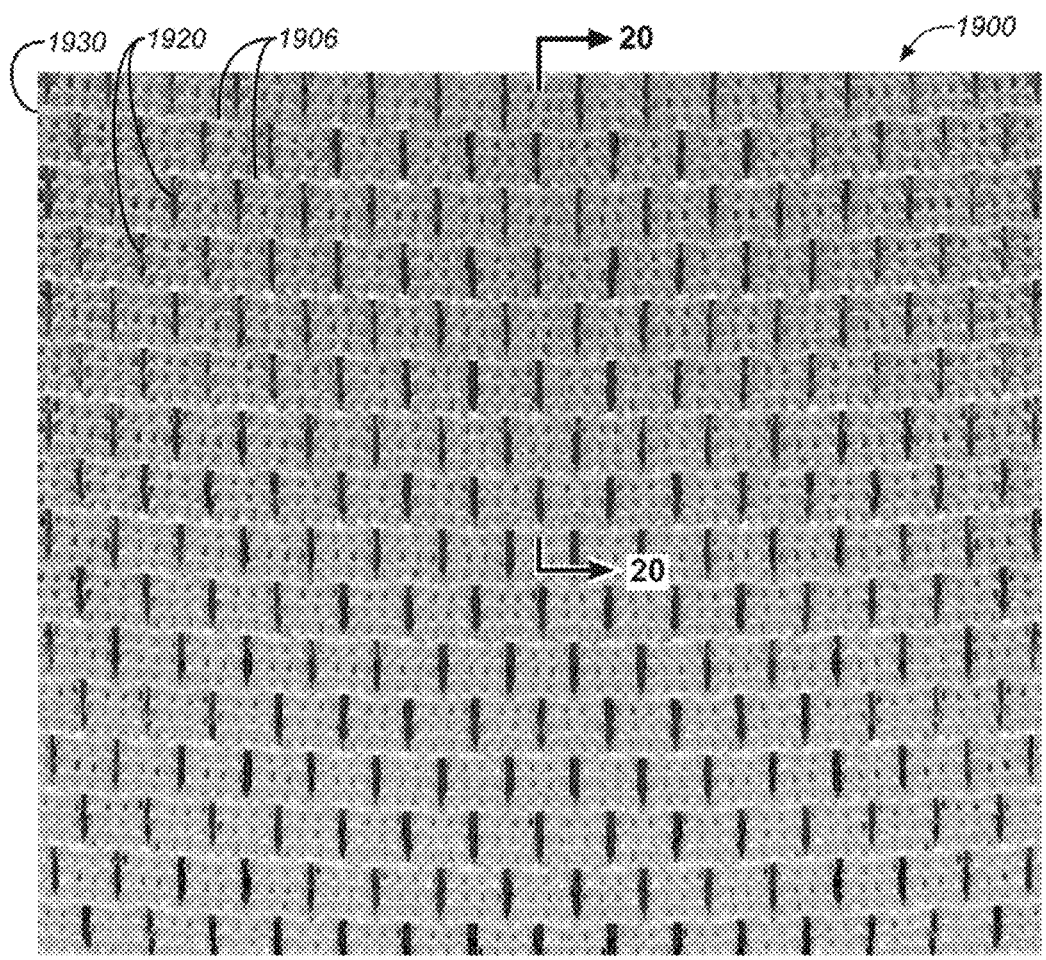
FIG. 19 is a top view of a honey impregnated gauze composite construction, used in the construction of the present invention.
Figure 20:
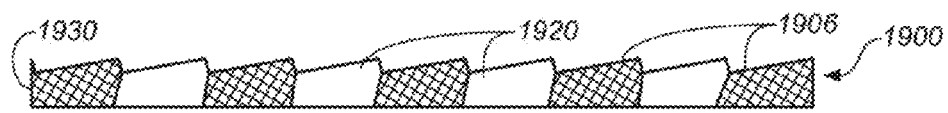
FIG. 20 is a cross-sectional view of a portion of the honey impregnated gauze composite construction, taken substantially along line 20-20 of FIG. 19.

Referring now to the drawings and more particularly to FIGS. 19 and 20, there is shown a honey-dosed or impregnated gauze construction 1900, which is constructed in accordance with the present invention. As described in more detail herein below, honey-dosed or impregnated gauze construction 1900 comprises a fabric material 1930, such as gauze, which contains gaps 1920 in the gauze 1930. The surface of the fabric 1930 is impregnated with honey (shown as areas 1906), such that the honey resides within the fabric 1930 between the gaps 1920 but substantially not in the gaps 1920. In order to promote healing of the wound 2704 (FIG. 29), the side of the honey-dosed or impregnated gauze construction 1900 containing the honey 1906 is placed on the wound 2704. The gauze construction 1900, preferably, has a weight of approximately 300 grams per meter squared. An anti-tackiness coating, sheet or protective layer (not shown) may or may not cover the honey.

As discussed above, honey impregnated gauze construction 1900 exhibits several advantages. As stated herein above, the gauze construction 1900 contains the honey within its structure. This particular structure of the gauze 1930 holds more honey than standard honey impregnated gauze dressings. The gaps 1920 in the gauze 1930 allow for greater expansion, conformity and flexibility of the gauze 1930. Furthermore, the gaps 1920 allow for the free passage of exudate, if present, within the wound, so that this may be more quickly collected and managed by any absorbent materials surrounding the wound treatment zone. Finally, as previously discussed herein, the high sugar levels found in the honey, result in an osmotic pressure that promotes autolytic debridement.

It is to be understood that gauze 1930 is woven, knitted or structured so as to define a plurality of laterally adjacent linear shaped gaps 1920 therein, illustrated with white background, as best seen in FIG. 20. Gaps 1920 form a regular pattern similar to the parallel walls between the cells on a honey comb. In this manner, honey impregnated gauze dressing 1900 forms a matrix that may be considered analogous to the structure of a bee's honey comb.

Honey 1906 is impregnated, preferably, by conventional immersion bath techniques, into fabric 1930 to completely fill the structure around the gaps 1920. For clarity of understanding the honey impregnated gauze construction 1900, the honey 1906 is shown in FIG. 20 as unobstructed shaded areas. The honey 1906 is used, among other things, to reduce the risk of wound infection and to promote healing, as with dressings 50, 150, 800 and 1500A, The preferred weight of honey dose for this presentation is between 65-70% of the total dressing weight.

Figure 22:
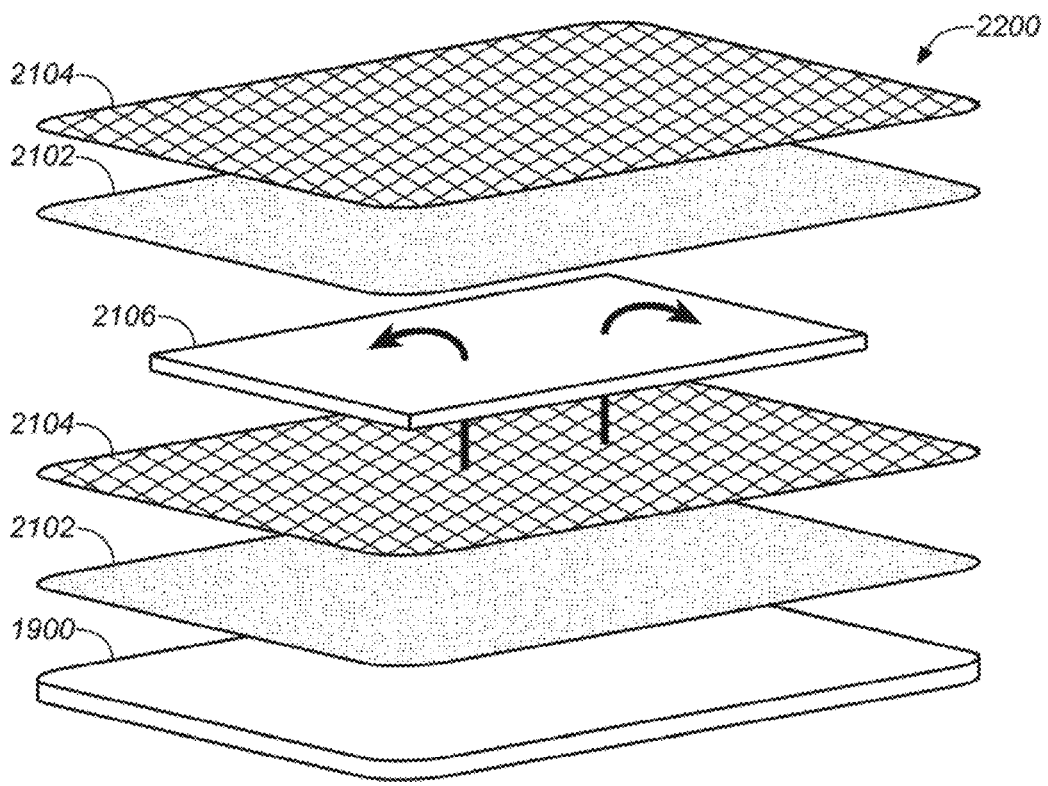
FIG. 22 is a schematic, exploded, perspective view of a honey impregnated gauze composite, forming part of the adherent honey-impregnated fabric wound dressing of FIGS. 26 and 27 and the non-adherent honey-impregnated fabric wound dressing of FIG. 28, which is used in the construction of the present invention.

Considering now the super absorbent, honey impregnated gauze composite 2200, in greater detail with reference to FIG. 22, the super absorbent, honey impregnated gauze composite 2200 generally includes a non-woven fabric layer 2104, a super absorbent panel layer 2106, another non-woven fabric layer 2104, and honey-impregnated gauze construction 1900. Non-woven fabric layers 2104 and super absorbent panel layer 2106 are constructed in the same manner as those described with respect to FIG. 21. Thermal bonding, via a hot melt thermal adhesive 2102, as described with respect to FIG. 21, is used to retain layers 2104, 2106, 2104, and 1900 in place. Note that non-woven fabric layers 2104 have a discontinuous hot-melt thermal adhesive coating 2102 conventionally applied to one face. Non-woven fabric layer 2104 also creates a barrier within the construction of the open weave fabric 1930 (FIG. 19) to prevent exudates (not shown) which accumulate in the super absorbent panel layer 2106 (FIG. 22) from travelling the opposite way into the wound. In the foam/fiber composite version, the foam/fiber structure 1514 performs this function, so the non-woven layer 2104 is only wicking and providing substance and structural integrity to the overall construction. Ideally, super absorbent panel 2106 will assist in drawing exudates away from honey-impregnated gauze construction 1900 so that honey-impregnated gauze construction 1900 does not become saturated with exudates. In this manner, super absorbent panel 2106 allows honey-impregnated gauze construction 1900 to remain very efficient in removing exudates from the wound area of the patient while allowing honey-impregnated gauze construction 1900 to continue to provide honey to the wound area.

Figure 21A:
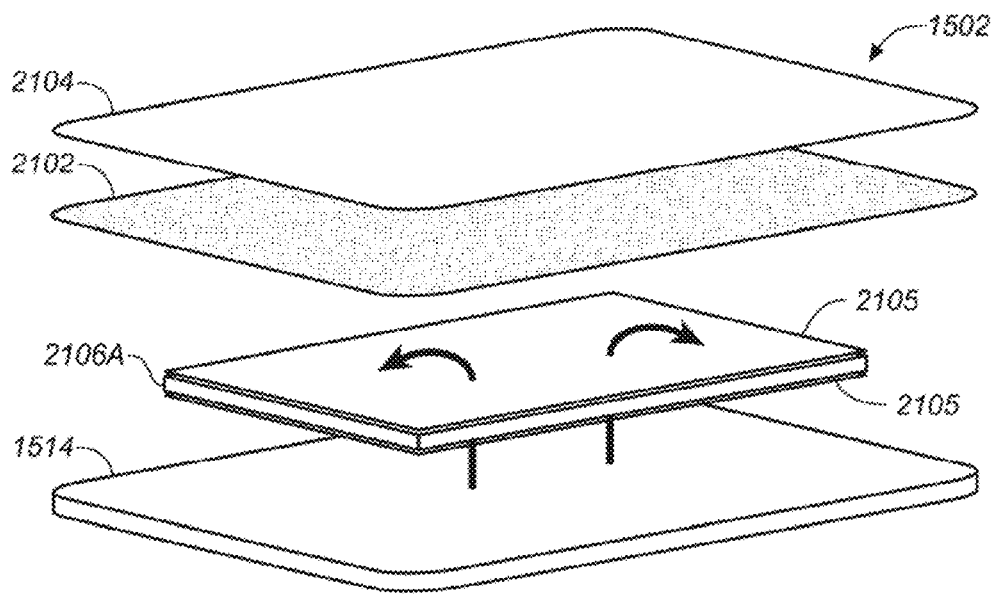
FIG. 21A is a schematic, exploded, perspective view of another honey-dosed, foam/fiber composite using super absorbent powder, forming part of the adherent honey-dosed, foam/fiber composite dressing of FIGS. 15A, 15B, and 16A and the non-adherent honey-dosed, foam/fiber composite dressing of FIGS. 15C, 15D, and 16B, which is constructed according to the present invention.
Figure 22A:
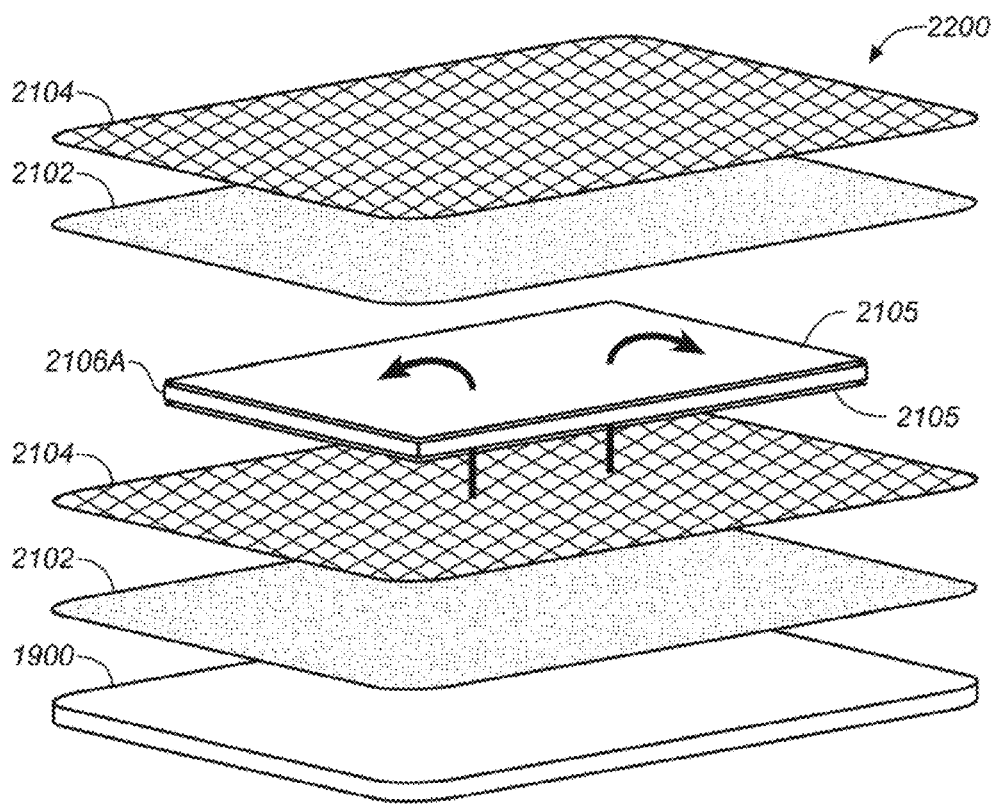
FIG. 22A is a schematic, exploded, perspective view of a honey impregnated gauze composite, using super absorbent powder, forming part of the adherent honey-impregnated fabric wound dressing of FIGS. 26 and 27 and the non-adherent honey-impregnated fabric wound dressing of FIG. 28, which is used in the construction of the present invention.

With respect to FIGS. 21A and 22A, in these embodiments, the super absorbent panel 2106 of FIGS. 21 and 22 has been replaced with a super absorbent powder layer 2106A. Preferably, the super absorbent powder is constructed of any conventional medical-grade, super absorbent powder that exhibits the same absorbent characteristics as those described with respect to super absorbent panel 2106. Located on either side of super absorbent powder layer 2106A are layers of tissue 2105. Tissue layers 2105, preferably, are constructed of medical-grade, wicking tissue that is capable of retaining the super absorbent powder layer 2106A while also providing wicking characteristics that prevent gel blocking and allow super absorbent powder layer 2106A to properly absorb the exudates from the patient's wound.

Considering now the adherent, super absorbent, honey-dosed foam/fiber composite dressing 1500, in greater detail with reference to FIGS. 15A, 15B and 23, the adherent, super absorbent, honey-dosed foam/fiber composite dressing 1500 generally includes a removable casting liner 2304, a bacterial barrier layer 1504, a honey-dosed foam/fiber composite construction 1502, and removable liners 1506 and 1508 having a fold 1507 conventionally constructed substantially along an edge of liner 1506. Casting liner 2304 can be used as a backing for bacterial barrier layer 1504 in order to provide structural integrity for bacterial barrier layer 1504. Casting liner 2304, preferably, is constructed of medical grade polyethylene. For some dressing presentations, casting liner 2304 can be left on, to provide support for bacterial barrier layer 1504 which is relatively thin and floppy. Bacterial barrier layer 1504, preferably, is a breathable barrier having a thickness range of about 20-30 microns. The bacterial barrier layer 1504 is composed of a sheet of breathable polyurethane. The purposes of bacterial barrier layer 1504 are to provide a barrier to stop bacterial infection from outside of the wound, to stop any honey 1510 from composite construction 1502 from potentially bleeding through bacterial barrier layer 1504, to protect the foam/fiber structure 1514 of composite construction 1502 from debris and liquid contamination, and to stop exudates from bleeding through the foam/fiber structure 1514 of composite construction 1502. It is to be understood that bacterial barrier layer 1504 is shown in FIGS. 23 and 24 as extending across the entire surface area of casting liner 2304. In this manner, bacterial barrier layer 1504 provides an adherent surface (skin compatible adhesive layer 1504A) that allows adherent dressing 1500A to be attached to a wound area of a patient, as will be described in greater detail later.

Preferably, removable liners 1506 and 1508 are constructed of any suitable medical grade polyethylene. Preferably, casting layer 2304 may be conventionally printed with arrows (not shown) and conventionally slit at 2302 with an air knife (not shown) to cause a partial separation from the bacterial barrier layer 1504 on either side of the slit 2302. This is done to assist the nurse during application of the dressing, as the dressing can be applied to the patient with the casting film 2304 still attached for ease of handling purposes, after which the casting film 2304 is removed and discarded. Without this, once the removable liners 1506 and 1508 (FIGS. 15A and 15B) have been removed from the adhesive side, the nurse would find the dressing almost impossible to handle and apply neatly to the patient's skin.

Referring now to the drawings, and more particularly to FIG. 24, there is shown another adherent type of honey-dosed or honey-impregnated composite wound dressing 2400 which is constructed in accordance with the present invention. This adherent type of honey-dosed composite wound dressing 2400 is identical in construction to the previously described adherent, honey-dosed composite wound dressing 1500 and will not be described hereinafter in greater detail except for identifying the differences between these embodiments.

Considering now the adherent type of honey-dosed composite wound dressing 2400 in greater detail with reference to FIG. 24, the composite wound dressing 2400 utilizes a highly skin sensitive type of adhesive gel 2402 that covers over the exposed portion of skin compatible adhesive layer 1504A. But for this difference in adhesives, the wound dressing 1500 and the wound dressing 2400 are identically constructed.

Gel layer 2402, preferably, is constructed of any suitable medical grade silicone gel. In this embodiment, silicone gel is used because it is a gentler adhesive that is particularly suited to patients with delicate or fragile skin.

Figure 25:
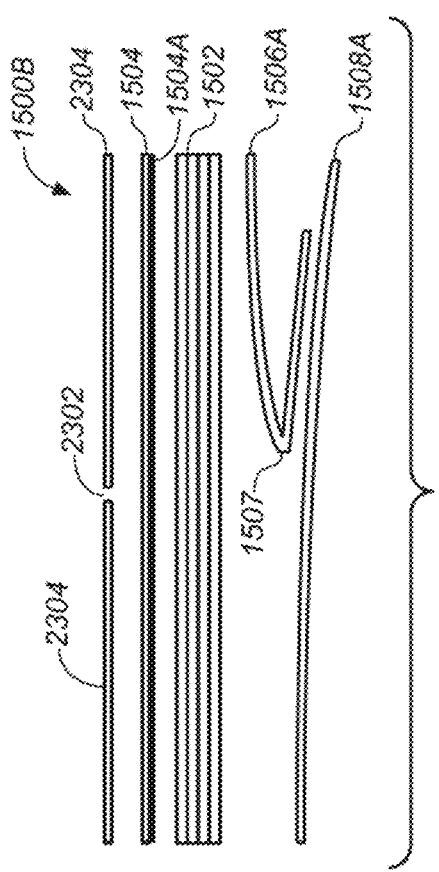
FIG. 25 is an exploded, side view of the non-adherent honey-dosed, foam/fiber composite dressing of FIGS. 15C and 15D.

Referring now to the drawings, and more particularly to FIG. 25, there is shown the non-adherent type of honey-dosed composite wound dressing 1500B (FIG. 16B). The non-adherent type honey-dosed composite wound dressing 1500B is constructed substantially the same as the adherent type of honey-dosed wound dressing 1500A and will not be described hereinafter in greater detail except for identifying the differences between these embodiments.

Considering now the non-adherent, honey-dosed composite wound dressing 1500B in greater detail with reference to FIG. 25, the composite wound dressing 1500B utilizes a smaller casting liner 2304 and smaller protective liners 1506A and 1508A which are sized to cover only the surface areas of the composite construction 1502. In this regard, the thin layer of adhesive 1504A provided on the bacterial barrier layer 1504 is utilized to only secure the bacterial barrier layer 1504 and its associated casting liner 2304 to the composite construction 1502. In a similar manner, the protective liners 1506A and 1508A are sized to cover the wound facing side of the composite construction 1502. But for these sizes differences, the adherent wound dressing 1500A and the non-adherent wound dressing 1500B have identical constructions.

Referring now to the drawings, and more particularly to FIG. 26, there is shown another adherent type of honey-dosed or honey-impregnated fabric wound dressing 2500 which is constructed in accordance with the present invention. This adherent type of honey-impregnated fabric wound dressing 2500 is substantially identical in construction to the previously described adherent, honey-dosed composite wound dressing 1500 and will not be described hereinafter in greater detail except for identifying the differences between these embodiments.

Referring now to the drawings, and more particularly to FIG. 26, there is shown another adherent type of honey-dosed or honey-impregnated fabric wound dressing 2500 which is constructed in accordance with the present invention. This adherent type of honey-impregnated fabric wound dressing 2500 is substantially identical in construction to the previously described adherent, honey-dosed composite wound dressing 1500 and will not be described hereinafter in greater detail except for identifying the differences between these embodiments.

Considering now the adherent type of honey-impregnated fabric wound dressing 2500 in greater detail with reference to FIG. 26, the fabric wound dressing 2500 utilizes a gauze composite 2200 instead of a composite construction 1502. But for this difference in composites, the wound dressing 1500 and the wound dressing 2500 are identically constructed.

As will be described in greater detail later, the layers of the gauze composite 2200 in the super absorbent, honey impregnated fabric dressing 2500A are held together by thermal bonding in the same manner as described earlier relative to the foam/fiber composite construction 1502. It is to be understood that bacterial barrier layer 1504 is shown in FIGS. 26 and 27 as extending across the entire surface area of casting liner 2304. In this manner, bacterial barrier layer 1504 with its thin of adhesive coating 1504A provides an adherent surface that allows dressing 2500A to be attached to a wound area of a patient, as will be described in greater detail later.

Referring now to the drawings, and more particularly to FIG. 27, there is shown another adherent type of honey-impregnated fabric wound dressing 2600 which is constructed in accordance with the present invention. This adherent type of honey-impregnated fabric wound dressing 2600 is identical in construction to the previously described adherent, honey-impregnated fabric wound dressing 2500 and will not be described hereinafter in greater detail except for identifying the differences between these embodiments.

Considering now the adherent type of honey-impregnated fabric wound dressing 2600 in greater detail with reference to FIG. 27, the fabric wound dressing 2600 utilizes a highly skin sensitive type of adhesive gel 2402 that covers over the exposed portion of skin compatible adhesive layer 1504A. But for this difference in adhesives, the fabric wound dressing 2500 and the fabric wound dressing 2600 are identically constructed it is to be understood that adhesive gel layer 2402 is substantially the same as discussed with respect to FIG. 24.

Figure 28:
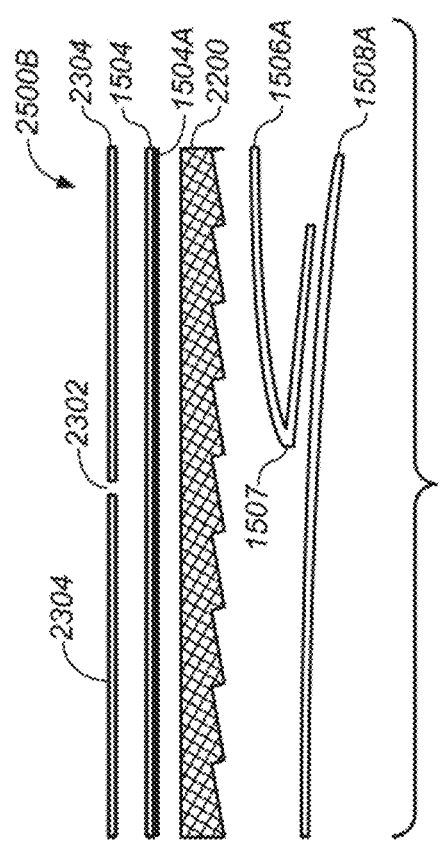
FIG. 28 is an exploded, side view of a non-adherent honey impregnated, gauze composite dressing, which is constructed according to the present invention.

Referring now to the drawings, and more particularly to FIG. 28, there is shown the non-adherent type of honey-impregnated fabric wound dressing 2500B. The non-adherent type honey-impregnated fabric wound dressing 2500B is constructed substantially the same as the adherent type of honey-impregnated fabric wound dressing 2500A and will not be described hereinafter in greater detail except for identifying the differences between these embodiments.

Considering now the non-adherent honey-impregnated fabric wound dressing 2500B in greater detail with reference to FIG. 28, the fabric wound dressing 2500B utilizes a smaller casting liner 2304 and smaller protective liners 1506A and 1508A which are sized to cover only the surface areas of the gauze composite 2200. In this regard, the thin layer of adhesive 1504A provided on the bacterial barrier layer 1504 is utilized to only secure the bacterial barrier layer 1504 and its associated casting liner 2304 to the gauze composite 2200. In a similar manner, the protective liners 1506A and 1508A are sized to cover the wound facing side of the gauze composite 2200. But for these sizes differences, the adherent wound dressing 2500A and the non-adherent wound dressing 2500B have identical constructions.

Considering now the application of super absorbent, honey-dosed foam/fiber composite dressing 1500A to a patient's wound, in greater detail with reference to FIGS. 15A, 15B, 16A, 23 and 29, the super absorbent, honey-dosed foam/fiber composite dressing 1500A has had its removable liners 1506 and 1508 (FIGS. 15A and 15B) conventionally peeled away or removed to expose super absorbent, honey-dosed foam/fiber composite dressing 1500A having a backing that includes casting liner 2304 and bacterial barrier layer 1504. The super absorbent, honey-dosed foam/fiber composite dressing 1500A is then placed over the wound area 2704 of the patient 2702. The thin adhesive layer 1504A (FIG. 23) secures the dressing 1500A to the skin of the patient at about the wound area 2704. It is to be understood that the difference between dressing 1500 and dressing 1500A is that removable liners 1506 and 1508 (or 1506A and 1508A) have been completely peeled away from composite construction 1502 in dressing 1500 in order to expose composite construction 1502 of dressing 1500A. It should also be understood that the use of the honey-dosed foam/fiber composition dressing 1500B is similar to the use of dressing 1500A except that a conventional, external adhesive tape (not shown) is needed to secure the dressing 1500B to the skin of the patient at about the wound area 2704.

Considering now the application to FIGS. 15A, 15B, 16A and 29, the super absorbent, honey-dosed foam/fiber composite dressing 1500 has had its removable liners (1506 and 1508 in FIGS. 15A and 15B or 1506A and 1506A in FIGS. 15C, 15D, 166 and 25) conventionally peeled away or removed to expose super absorbent, honey-dosed foam/fiber composite dressing 1500A. The super absorbent, honey-dosed foam/fiber composite dressing 1500A is then placed over the wound area 2704 of the patient 2702. It is to be understood that the difference between dressing 1500 and dressing 1500A is that removable liners 1506 and 1508 (or 1506A and 1508A) have been completely peeled away from composite construction 1502 in dressing 1500 in order to expose composite construction 1502 of dressing 1500A.

As discussed above, in this manner, dressing 1500A is constructed to provide super absorbency by pulling or drawing exudates from wound area 2704 into the dressing 1500A through the use of a super absorbent panel (or super absorbent powder, as described with respect to FIG. 21A) and dispersing a precise amount of honey 1510 from the dressing 1500A throughout the treatment zone of wound 2704. In particular, the patterns of honey-dosed composite areas 1552 and the patterns of non-dosed gaps 1512, as best seen in FIGS. 17 and 18, cooperate with one another to create a pumping, push-pull action that allows the dressing 1500A to: 1) absorb or pull wound exudates from a treated wound area 2704 into the non-dosed gaps 1512; and 2) to disperse substantially the totality of the honey 1510 in the honey-dosed areas 1552 onto the treated wound area 2704 covered by dressing 1500A.

Figure 30:
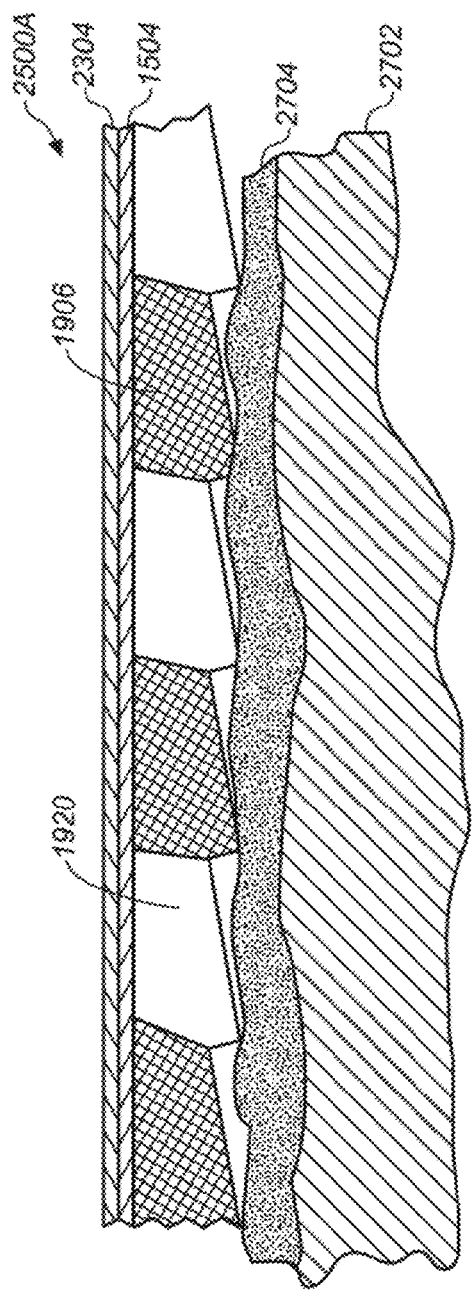
FIG. 30 is a schematic illustration of the honey impregnated gauze composite dressing of FIG. 26, being applied to a wound, according to the present invention.

Considering now the application of super absorbent, honey impregnated fabric dressing 2500A to a patient's wound, in greater detail with reference to FIGS. 20 and 30, the super absorbent, honey impregnated fabric dressing 2500 first has its removable liners 1506 and 1508 conventionally peeled away or removed, as discussed above with reference to FIG. 29, in order to create super absorbent, honey impregnated fabric dressing 2500A having a backing that includes casting liner 2304 and bacterial barrier layer 1504. The super absorbent, honey impregnated fabric dressing 2500A is then placed over the wound area 2704 of the patient 2702. It is to be understood that the difference between dressing 2500 and dressing 2500A is that removable liners 1506 and 1508 have been completely peeled away from honey impregnated fabric composite 2200 in dressing 2500 in order to expose honey impregnated fabric composite 2200 of dressing 2500A.

As discussed above, in this manner, dressing 2500A is constructed to provide super absorbency by pulling or drawing exudates from wound area 2704 into the dressing 2500A through the use of a super absorbent panel and dispersing a precise amount of honey 1906 from the dressing 2500A throughout the treatment zone of wound 2704. As discussed above, dressing 2500A holds more honey 1906 than standard honey impregnated gauze dressings. The gaps 1920 in the gauze 1930 allow for greater expansion, conformity and flexibility of the dressing 2500A. Furthermore, the gaps 1920 allow for the free passage of exudate, if present, within the wound 2704, so that this may be more quickly collected and managed by any absorbent materials surrounding the wound treatment zone. Finally, as previously discussed herein, the high sugar levels found in the honey, result in an osmotic pressure that promotes autolytic debridement.

As discussed above, in this manner, dressing 2500A can also be constructed to provide super absorbency by pulling or drawing exudates from wound area 2704 into the dressing 2500A through the use of a super absorbent powder, as described with respect to FIG. 22A and dispersing a precise amount of honey 1906 from the dressing 2500A throughout the treatment zone of wound 2704. As discussed above, dressing 2500A holds more honey 1906 than standard honey impregnated gauze dressings. The gaps 1920 in the gauze 1930 allow for greater expansion, conformity and flexibility of the dressing 2500A. Furthermore, the gaps 1920 allow for the free passage of exudate, if present, within the wound 2704, so that this may be more quickly collected and managed by any absorbent materials surrounding the wound treatment zone. Finally, as previously discussed herein, the high sugar levels found in the honey, result in an osmotic pressure that promotes autolytic debridement.

Figure 31:
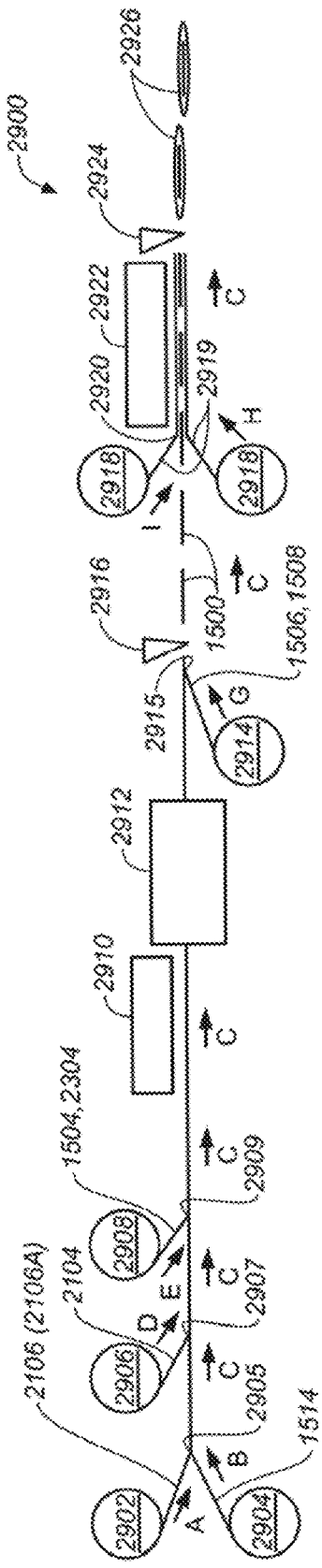
FIG. 31 is a schematic illustration of the construction of a honey-dosed, foam/fiber composite super absorbent dressing, constructed according to the present invention.
Figure 32:
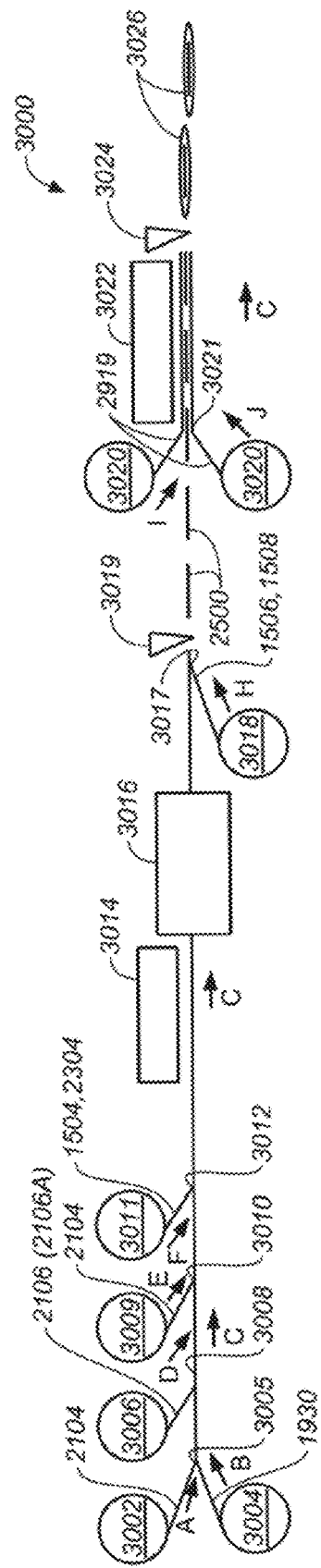
FIG. 32 is a schematic illustration of the construction of a honey impregnated, gauze, super absorbent dressing, constructed according to the present invention.

Referring the drawings and more particularly to FIG. 31, a dressing construction apparatus 2900 is illustrated, which apparatus 2900 is constructed in accordance with the present invention. The apparatus 2900 forms ribbons of super absorbent, honey-dosed foam/fiber dressings which are cut to a predetermined length and then packaged by means (not shown) for shipping purposes. In this regard, the results provide individually packaged, super absorbent honey-dosed foam/fiber dressings 2926.

Considering now the method of constructing the individually packaged, super absorbent, honey-dosed foam/fiber dressings 2926 in greater detail, the apparatus 2900 generally includes a first set of feed rollers indicated at 2902 and 2904, respectively. Feed roller 2902 pulls into a construction path (A) cut pieces or portions of super absorbent panel material 2106 (or super absorbent powder 2106A, as described with respect to FIG. 21A) from a spool of super absorbent panel material (or super absorbent powder material). The pieces of super absorbent panel material 2106 (or super absorbent powder 2106A) have a width dimension required for the dressing 1500. Feed roller 2904 pulls into another construction path (B), a ribbon of foam/fiber composite structure material 1514, whose width dimension is larger than the width dimension of the pieces of super absorbent panel material 2106 (or super absorbent powder 2106A). The A construction path and the B construction path merge at a nip 2905 and traverse along the direction of arrow C.

Feed roller 2906 pulls into a construction path (D) a ribbon of non-woven fabric 2104 from a spool of non-woven fabric such that the ribbon of non-woven fabric 2104 is placed over the pieces of super absorbent panel material 2106 (or super absorbent powder 2106A) and foam/fiber structure material 1514 such that the ribbon of non-woven fabric 2104 is placed directly over the pieces of super absorbent panel material 2106 (or super absorbent powder 2106A). The ribbon of non-woven fabric 2104 has a width dimension required for the dressing 1500. The C construction path and the D construction path merge at a nip 2907 and traverse along the direction of arrow C.

Feed roller 2908 pulls into a construction path (E) a ribbon of bacterial barrier film 1504 and casting liner 2304 from a spool of bacterial barrier film and casting liner such that the ribbon of bacterial barrier film 1504 and casting liner 2304 is placed over the ribbon of pieces of super absorbent panel material 2106 (or super absorbent powder 2106A), foam/fiber structure material 1514, and non-woven fabric 2104 such that the ribbon of bacterial barrier film 1504 and casting liner 2304 is placed directly over the ribbon of non-woven fabric 2104. The ribbon of bacterial barrier film 1504 and casting liner 2304 has a width dimension required for the dressing 1500. It is to be understood that the width of bacterial barrier film 1504 and casting liner 2304 can vary depending upon whether it is desired to cover the entire surface area of dressing 1500 or just the surface area of foam/fiber structure material 1514, as discussed above with respect to FIGS. 23-25. The C construction path and the E construction path merge at a nip 2909 and traverse along the direction of arrow C.

A heated platen 2910 is in close proximity with the ribbon of pieces of super absorbent panel material 2106 (or super absorbent powder 2106A), foam/fiber structure material 1514, non-woven fabric 2104, bacterial barrier film 1504, and casting liner 2304. The heat from platen 2910 creates thermal bonding which causes the ribbon of pieces of super absorbent panel material 2106 (or super absorbent powder 2106A), foam/fiber structure material 1514, non-woven fabric 2104, bacterial barrier film 1504, and casting liner 2304 to become thermally bonded together.

After the ribbon of pieces of super absorbent panel material 2106 for super absorbent powder 2106A), foam/fiber structure material 1514, non-woven fabric 2104, bacterial barrier film 1504, and casting liner 2304 are thermally bonded together, honey (not shown) is applied to the ribbon of pieces super absorbent panel material 2106 (or super absorbent powder 2106A), foam/fiber structure material 1514, non-woven fabric 2104, bacterial barrier film 1504, and casting liner 2304 by honey applicator 2912. In particular, honey is dosed in foam/fiber structure material 1514, such that the side of foam/fiber structure material 1514 which faces away from the pieces of super absorbent panel material 2106 for super absorbent powder 2106A) is partially dosed with honey, as described earlier.

Feed roller 2914 pulls into a construction path (G) a ribbon of high density polyethylene liners 1506, 1508 from a spool of high density polyethylene liners such that the ribbon of high density polyethylene liners 1506, 1508 is placed over the heat sealed ribbon of pieces of super absorbent panel material 2106 (or super absorbent powder 2106A), honey-dosed, foam/fiber structure material 1514, non-woven fabric 2104, bacterial barrier layer 1504, and casting liner 2304, such that the ribbon of polyethylene liners 1506, 1508 is placed directly over the ribbon of honey-dosed, foam/fiber structure material 1514. The ribbon of polyethylene liners 1506, 1508 has a width dimension required for the dressing 1500. Also, fold 1507, as shown in FIGS. 23-25 is conventionally constructed at this location. The C construction path and the G construction path merge at a nip 2915 and traverse along the direction of arrow C.

Next, the heat sealed ribbon of pieces of super absorbent panel material 2106 (or super absorbent powder 2106A), honey-dosed, foam/fiber structure material 1514, non-woven fabric 2104, bacterial barrier 1504, and casting liner 2304, and polyethylene liners 1506, 1508 is conventionally cut by cutter 2916 to create super absorbent, honey-dosed foam/fiber dressing 1500.

After super absorbent, honey-dosed foam/fiber dressings 1500 are created, feed rollers 2918 pull into construction paths (H and I) ribbons of pouch film 2919 from spools of pouch film such that the ribbons of pouch film 2919 are placed over and under the super absorbent, honey-dosed foam/fiber dressings 1500. Preferably, pouch film 2919 is constructed of any suitable heat sealable, medical grade polymeric film. The C construction path and the H and I construction paths merge at a nip 2920 and traverse along the direction of arrow C.

A heated platen 2922 is in close proximity with the ribbons of pouch film 2919 and super absorbent, honey-dosed foam/fiber dressings 1500. The heat from platen 2922 creates thermal bonding which causes the ribbons of pouch film 2919 to become thermally bonded together thereby enclosing the super absorbent, honey-dosed foam/fiber dressings 1500.

The heat sealed ribbon of pouch film 2919 and super absorbent, honey-dosed foam/fiber dressings 1500 is conventionally cut by cutter 2924 to create individually packaged, super absorbent, honey-dosed foam/fiber dressing packages 2926. Once this final cut is completed, super absorbent, honey-dosed foam/fiber dressing packages 2926 pass through a conventional metal detector and inspection protocol. Finally, after the metal detector and inspection protocol are completed, packages 2926 are packed and conventionally gamma irradiated for final release.

Considering now the method of constructing the individually packaged, super absorbent, honey impregnated gauze dressings 3026 in greater detail, the apparatus 3000 generally includes a first set of feed rollers indicated at 3002 and 3004, respectively. Feed roller 3002 pulls into a construction path (A) a ribbon of non-woven fabric 2104 from a spool of non-woven fabric. The ribbon of non-woven fabric 2104 has a width dimension required for the dressing 2500. Feed roller 3004 pulls into another construction path (B), a ribbon of gauze material 1930, whose width dimension corresponds to the width dimension of the ribbon of non-woven fabric 2104. The A construction path and the B construction path merge at a nip 3005 and traverse along the direction of arrow C.

Feed roller 3006 pulls into a construction path (D) a ribbon of pieces or portions of super absorbent panel material 2106 (or super absorbent powder 2106A) from a spool of super absorbent panel material (or super absorbent powder material) such that the cut pieces of super absorbent panel material 2106 (or super absorbent powder 2106A) are placed over the ribbon of non-woven fabric 2104 and gauze material 1930 such that the pieces of super absorbent panel material 2106 (or super absorbent powder 2106A) are placed directly over the ribbon of non-woven fabric 2104. The pieces of super absorbent panel material 2106 (or super absorbent powder 2106A) have a width dimension required for the dressing 2500. The C construction path and the D construction path merge at a nip 3008 and traverse along the direction of arrow C.

Feed roller 3009 pulls into a construction path (E) a second ribbon of non-woven fabric 2104 from a second spool of non-woven fabric such that the second ribbon of non-woven fabric 2104 is placed over the ribbon of non-woven fabric 2104, gauze material 1930, and pieces of super absorbent panel material 2106 (or super absorbent powder 2106A) such that the second ribbon of non-woven fabric 2104 is placed directly over the pieces of super absorbent panel material 2106 (or super absorbent powder 2106A). The second ribbon of non-woven fabric 2104 has a width dimension required for the dressing 2500. The C construction path and the E construction path merge at a nip 3010 and traverse along the direction of arrow C.

Feed roller 3011 pulls into a construction path (F) a ribbon of bacterial barrier film 1504 and casting liner 2304 from a spool of bacterial barrier film and casting liner such that the ribbon of bacterial barrier film 1504 and casting liner 2304 is placed over the ribbon of non-woven fabric 2104, gauze material 1930, pieces of super absorbent panel material 2106 for super absorbent powder 2106A), and the non-woven fabric 2104 such that the ribbon of bacterial barrier film 1504 and casting liner 2304 is placed directly over the second ribbon of non-woven fabric 2104. The ribbon of bacterial barrier film 1504 and casting liner 2304 has a width dimension required for the dressing 2500. The C construction path and the F construction path merge at a nip 3012 and traverse along the direction of arrow C.

A heated platen 3014 is in close proximity with the ribbon of non-woven fabric 2104, gauze material 1930, pieces of super absorbent panel material 2106 (or super absorbent powder 2106A), the non-woven fabric 2104, bacterial barrier film 1504, and casting liner 2304. The heat from platen 3014 creates thermal bonding which causes the ribbon of non-woven fabric 2104, gauze material 1930, pieces of super absorbent panel material 2106 for super absorbent powder 2106A), non-woven fabric 2104, bacterial barrier film 1504, and casting liner 2304 to become thermally bonded together.

After the ribbon of non-woven fabric 2104, gauze material 1930, pieces of super absorbent panel material 2106 (or super absorbent powder 2106A), non-woven fabric 2104, bacterial barrier film 1504, and casting liner 2304 are thermally bonded together, honey is applied to the ribbon of non-woven fabric 2104, gauze material 1930, super absorbent panel material 2106 (or super absorbent powder 2106A), non-woven fabric 2104, bacterial barrier film 1504, and casting liner 2304 by honey applicator 3016, In particular, honey (not shown) is impregnated into gauze material 1930, such that the side of gauze material 1930 which faces away from the first ribbon of non-woven fabric 2104 is impregnated with honey, as described earlier.

Feed roller 3018 pulls into a construction path (H) a ribbon of high density polyethylene liners 1506, 1508 from a spool of high density polyethylene liners such that the ribbon of high density polyethylene liners 1506, 1508 is placed over the heat sealed ribbon of non-woven fabric 2104, honey impregnated gauze material 1930, super absorbent panel material 2106 (or super absorbent powder 2106A), non-woven fabric 2104, bacterial barrier film 1504, and casting liner 2304, such that the ribbon of high density polyethylene liners 1506, 1508 is placed directly over the ribbon of honey impregnated gauze material 1930, The ribbon of high density polyethylene liners 1506, 1508 has a width dimension required for the dressing 2500. Also, the fold described with respect to FIGS. 26-28 is constructed at this location. The C construction path and the H construction path merge at a nip 3017 and traverse along the direction of arrow C.

Next, the heat sealed ribbon of non-woven fabric 2104, honey impregnated gauze material 1930, super absorbent panel material 2106 (or super absorbent powder 2106A), non-woven fabric 2104, bacterial barrier layer 1504, and casting liner 2304 and high density polyethylene liners 1506, 1508 having fold 1507 is conventionally cut by cutter 3019 to create super absorbent, honey impregnated fabric dressing 2500.

After super absorbent, honey impregnated fabric dressings 2500 are created, feed rollers 3020 pull into construction paths (i and J) ribbons of pouch film 2919 from spools of pouch film such that the ribbons of pouch film 2919 are placed over and under the super absorbent, honey impregnated fabric dressings 2500. Preferably, pouch film 2919 is constructed of any suitable heat sealable, medical grade polymeric film. The C construction path and the I and J construction paths merge at a nip 3021 and traverse along the direction of arrow C.

A heated platen 3022 is in close proximity with the ribbon of pouch film 2919 and super absorbent, honey impregnated fabric dressings 2500. The heat from platen 3022 creates thermal bonding which causes the ribbons of pouch films 2919 to become thermally bonded together thereby enclosing the super absorbent, honey impregnated fabric dressings 2500.

The heat sealed ribbon of pouch film 2919 and super absorbent, honey impregnated fabric dressings 2500 is conventionally cut by cutter 3024 to create individually packaged, super absorbent, honey impregnated fabric dressing packages 3026. Once this final cut is completed, super absorbent, honey impregnated fabric packages 3026 pass through a conventional metal detector and inspection protocol. Finally, after the metal detector and inspection protocol are completed, packages 3026 are packed and conventionally gamma irradiated for final release.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents to the extent such incorporated materials and information are not inconsistent with the description herein.

The written description portion of this patent includes all claims. Furthermore, all claims, including all original claims as well as all claims from any and all priority documents, are hereby incorporated by reference in their entirety into the written description portion of the specification, and Applicant(s) reserve the right to physically incorporate into the written description or any other portion of the application, any and all such claims, Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended and those skilled in the art will recognize, that the invention embraces and is also thereby described in terms of any individual member or subgroup of members of the Markush group.

Other embodiments are within the following claims. There ore the patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

Other modifications and implementations will occur to those skilled in the art without departing from the spirit and the scope of the invention as claimed. Accordingly, the description hereinabove is not intended to limit the invention, except as indicated in the appended claims.

Therefore, provided herein are a new and improved honey impregnated, patterned foam dressing and a novel method of using the honey impregnated, patterned foam dressing. The preferred honey impregnated, patterned foam dressing, according to various embodiments of the present invention, offers the following advantages: ease of use; improved dressing strength; reduced dressing weight; increased efficiency and controlled lay down of honey; increased ability to deliver an equal measure of honey across the wound bed; increased ability to promote controlled, naturally occurring osmotic delivery action of the honey onto the wound bed; increased rate of absorption of exudates while allowing honey stored within the honey-dosed area to flow naturally onto the wound; improved ease of handling of the dressing; intelligent management of exudates through the foam/fiber composite into the super absorbent panel; the honey is dispersed faster and more evenly into the wound; dressing liners allow for easy handling of the dressing and protect dressing from accidental damage; improved odor control, and the single-sided application of honey to dressing presents the honey dose to the wound face of dressing rather than wasting unused honey on the bandage side of dressing. In fact, in many of the preferred embodiments, these factors of improved strength, reduced weight, increased lay down efficiency, increased honey loading, increased honey delivery, increased osmotic delivery action, increased exudate absorption ability, improved ease of handling, intelligent management of exudates, honey dispersion; the use of dressing liners, odor control, and the single-sided application of honey to the dressing are optimized to an extent that is considerably higher than heretofore achieved in prior, known honey-based wound dressings.

We claim:

1. A super absorbent, honey-dosed foam/fiber composite, gap patterned wound dressing, comprising:
   a patterned foam/fiber composite structure having a gap patterned side and a non-gap patterned side, wherein the patterned side includes a pattern of foam/fiber gaps disposed between foam/fiber areas dosed with honey, where the pattern of foam/fiber gaps is formed by the honey-dosed areas, such that the patterned foam/fiber composite structure includes a layer of super absorbent material located substantially adjacent to the honey-dosed areas; and wherein a wound in contact with the gap patterned side discharges an exudate which substantially collects in the individual ones of the foam/fiber gaps causing honey in the individual ones of the honey-dosed areas to be substantially dispersed throughout a wound treatment zone and a portion of the exudate that is collected in the individual ones of the foam/fiber gaps is transferred to and collected in the super absorbent material.

2. The wound dressing, as in claim 1, wherein the individual ones of the honey-dosed areas are hexagon-shaped areas.

3. The wound dressing, as in claim wherein the super absorbent material is a medical-grade, super absorbent polymer.

4. The wound dressing, as in claim 1, wherein the super absorbent material is a medical-grade, super absorbent powder.

5. The wound dressing, as in claim 1, wherein the wound dressing is further comprised of:
a bacterial barrier layer having a proximal side and a distal side wherein the non-gap patterned side of the patterned foam/fiber composite is located substantially adjacent to the proximal side of the bacterial barrier layer.

6. The wound dressing, as in claim 5, wherein the bacterial barrier layer is a medical-grade, breathable polyurethane film material which has an adhesive coating substantially applied to the proximal side.

7. The wound dressing, as in claim 5, wherein the wound dressing is further comprised of:
a removable liner located substantially adjacent to the distal side of the bacterial barrier layer.

8. The wound dressing, as in claim 7, wherein the removable liner is a medical grade polyethylene.

9. The wound dressing, as in claim 5, wherein the wound dressing is her comprised of:
a removable liner located substantially adjacent to the proximal side of the bacterial barrier layer and substantially enclosing the patterned foam/fiber composite, wherein the removable liner is a medical grade, high density polyethylene.

10. The wound dressing, as in claim 5, wherein the wound dressing is further comprised of:
a gel adhesive layer wherein the gel adhesive layer is located substantially adjacent to the foam/fiber composite and the proximal side of the bacterial barrier layer.

11. The wound dressing, as in claim 10, wherein the gel adhesive layer is a silicone gel adhesive.

12. The wound dressing, as in claim 1, wherein the patterned foam/fiber composite structure is comprised of a thickness in a range of between 0.05 mm to about 100 mm.

* * * * *